United States Patent [19]
Prichard et al.

[11] Patent Number: 6,114,376
[45] Date of Patent: Sep. 5, 2000

[54] METHODS FOR USING MACROCYCLIC LACTONE COMPOUNDS AS MULTIDRUG RESISTANCE REVERSING AGENTS IN TUMOR AND OTHER CELLS

[75] Inventors: Roger K. Prichard, Beaconsfield; Jean-François Pouliot, Montreal; Elias Georges, Chomedy, all of Canada

[73] Assignee: McGill University, Montreal, Canada

[21] Appl. No.: 09/067,677

[22] Filed: Apr. 28, 1998

Related U.S. Application Data

[60] Provisional application No. 60/045,161, Apr. 30, 1997.

[51] Int. Cl.[7] .................................................. A61K 31/335
[52] U.S. Cl. ............................................................. 514/450
[58] Field of Search ............................................. 514/450

[56] References Cited

U.S. PATENT DOCUMENTS

| | | | |
|---|---|---|---|
| 3,950,360 | 4/1976 | Aoki et al. | 549/264 |
| 4,199,569 | 4/1980 | Chabala et al. | 514/30 |
| 4,310,519 | 1/1982 | Albers-Schonberg et al. | 514/30 |
| 4,916,154 | 4/1990 | Asato et al. | 514/450 |
| 5,106,994 | 4/1992 | Carter et al. | 549/264 |
| 5,169,956 | 12/1992 | Carter et al. | 549/264 |
| 5,578,637 | 11/1996 | Lai et al. | 514/540 |

FOREIGN PATENT DOCUMENTS

| | | |
|---|---|---|
| 4-235126 A2 | 8/1992 | Japan . |
| 94/22846A1 | 10/1994 | WIPO . |
| 96/01127A1 | 1/1996 | WIPO . |

OTHER PUBLICATIONS

Pouliot et al., Reversal of P–Glycoprotein–Associated Multidrug Resistance by Ivermectin, Biochem. Pharm. 53(1):17–25 (Jan. 10, 1997).

Greenwald et al., Mechanistic Studies of Passive and Active Transport Processes in MDCK Cells: Transport of Selected Anthelmintics, oral presentation at 41st Annual Meeting, Jul. 20–23, 1996 (KY) AAVP Proceedings abstr. 12.

Didier et al., The abamectin derivative ivermectin is a potent P–glycoprotein inhibitor, Anti–Cancer Drugs 7:745–751 (1996).

Didier et al., Decreased uptake of cyclosporin A by P–glycoprotein (Pgp) expressing CEM leukemic cells & restoration of normal retention by Pgp blockers, Anti–Cancer Drugs 6:669–680 (1995).

Didier et al., Decreased biotolerability for ivermectin & cyclosporin A in mice exposed to potent P–glycoprotein inhibitors, Int. J. Cancer 63:263–267 (1995).

Schinkel et al., Disruption of the Mouse mdr1a P–Glycoprotein Gene Leads to a Deficiency in the Blood–Brain Barrier and to Increased Sensitivity to Drugs, Cell 77:491–502 (May 20, 1994).

*Primary Examiner*—Kathleen K. Fonda
*Attorney, Agent, or Firm*—Anne M. Rosenblum

[57] ABSTRACT

This invention describes methods for increasing the toxicity of a cytostatic hydrophobic chemotherapeutic agent against resistant tumor cells in mammals which comprise administering a multidrug resistant reversing agent to the mammal in connection with the administration of the cytostatic hydrophobic chemotherapeutic agent in an amount effective to increase the toxicity of the chemotherapeutic agent, wherein the multidrug resistant reversing agent is a macrocyclic lactone compound. Examples of the macrocyclic lactone compounds useful in the present invention include, but are not limited to, the LL-F28249α-λ series of compounds, the 23-oxo or 23-imino derivative thereof, the avermectins, the 22,23-dihydro derivatives thereof and the milbemycins. Compositions comprising the macrocyclic lactone compounds and the chemotherapeutic agents are also described herein.

15 Claims, 11 Drawing Sheets

METHODS FOR USING MACROCYCLIC LACTONE COMPOUNDS AS MULTIDRUG RESISTANCE REVERSING AGENTS IN TUMOR AND OTHER CELLS

RELATED U.S. APPLICATION DATA

This application claims the benefit under 35 U.S.C. § 119(e) of U.S. Provisional application Ser. No. 60/045,161, filed Apr. 30, 1997.

BACKGROUND OF THE INVENTION

1. Field of the Invention

This invention relates generally to novel methods for enhancing the biological activity of chemotherapeutic agents. More specifically, the invention pertains to unique methods for increasing the toxicity of cytostatic hydrophobic chemotherapeutic agents using multidrug resistant reversing agents in which the multidrug resistant reversing agents are macrocyclic lactone compounds.

2. Description of Related Art

Selection of tumor cells with cytostatic hydrophobic drugs has been shown to result in the development of a multidrug resistance (mdr) phenotype and in the overexpression of P-glycoprotein (Pgp) (Gottesman et al., Biochemistry of multidrug resistance mediated by the multidrug transporter, *Annu. Rev. Biochem.* 62: 385–427, 1993; Endicott et al., The biochemistry of P-glycoprotein-mediated multidrug resistance, *Annu. Rev. Biochem.* 58: 137–171, 1989). Pgp is a member of the ABC (ATP binding cassette) superfamily of membrane transporters that includes the multidrug resistance associated protein MRP (Cole et al., Pharmacological characterization of multidrug resistant MRP-transfected human tumor cells, *Cancer Res.* 54: 5902–5910, 1994), the cystic fibrosis transmembrane conductance regulator (CFTR) (Riordan et al., Amplification of P-glycoprotein genes in multidrug-resistant mammalian cell lines, *Nature* 316: 817–819, 1985) and several bacterial periplasmic membrane proteins (Higgins, ABC transporters: from microorganisms to man, *Annu. Rev. Cell Biol.* 8: 67–113, 1992). Although Pgp has been shown to cause multidrug resistance (MDR) in tumor cells, its function in normal tissues is less certain. Pgp gene family in rodents and humans consists of three classes (I, II, and III) and two classes (I and III), respectively. Moreover, while classes I and II have been shown to cause MDR, class III of both rodents and humans does not. Using homologous recombination, it was shown that class I Pgp is involved in drug transport in normal tissues while class III Pgp mediates phosphatidyl-choline transport (Smit et al., Homozygous disruption of the murine mdr2 P-glycoprotein gene leads to a complete absence of phospholipid from bile and to liver disease, *Cell* 75: 451–462, 1993) and may be "a flipase" (Ruetz et al., Phosphatidyl-choline translocase—a physiological role for the mdr2 gene, *Cell* 77: 1071–1081, 1994).

Various levels of Pgp expression have been shown in tumors from different cancers (Goldstein et al., Expression of a multidrug resistance gene in human cancers, *J. Natl. Cancer Inst.* 81: 116–124, 1989). However, more studies are needed to determine if changes in Pgp levels in tumor cells are prognostic of MDR. Recently, Pgp expression in sarcomas of children and neuroblastomas was shown to correlate with low response to chemotherapy and the long term survival of patients (Chan et al., Multidrug resistance in pediatric malignancies, *Hematol. Oncol. Clin. North Am.* 9: 275–318, 1995; Chan et al., P-glycoprotein expression as a predictor of the outcome of therapy for neuroblastoma, *N. Engl. J. Med.* 325: 1608–1614, 1991). Other studies using MDR-reversing drugs have implicated Pgp in some MDR cancers (Ford, MODULATORS OF MULTIDRUG RESISTANCE, Preclinical Studies, *Hematol. Oncol. Clin. North Am.* 9: 337–361, 1995; Ozols, Clinical reversal of drug resistance—foreword, *Curr. Probl. Cancer* 19: 69–123, 1995; Patel et al., Multidrug resistance in cancer chemotherapy, *Invest. New Drugs* 12: 1–13, 1994). Nevertheless, a clear clinical benefit of MDR-reversing drugs remains to be demonstrated. Earlier attempts to use verapamil as an MDR-reversing drug have been hampered by its high cardiotoxicity (Dalton et al., A phase III randomized study of oral verapamil as a chemosensitizer to reverse drug resistance in patients with refractory myeloma, *Cancer* 75: 815–820, 1995; Pennock et al., Systemic toxic effects associated with high-dose verapamil infusion and chemotherapy administration, *J. Natl. Cancer Inst.* 83: 105–110, 1991). In tumoral lymphoid (CEM) cells, one study showed a higher retention of cyclosporin A (CsA) in Pgp-lacking parental cells than in Pgp-expressing MDR cells leading the authors to believe that Pgp blockers could restore CsA retention in the MDR-CEM cells (Didier et al., Decreased uptake of cyclosporin A by P-glycoprotein (Pgp) expressing CEM leukemic cells and restoration of normal retention by Pgp blockers, *Anti-cancer Drugs*, 6: 669–680, 1995). While the results obtained with cyclosporin A and the non-immunosuppressive analog SDZ-PSC 833 have been encouraging, some toxic effects were also observed when cyclosporin A was used in clinical studies (Warner et al., Phase I–II study of vinblastine and oral cyclosporin A in metastatic renal cell carcinoma, *Am. J. Clin. Oncol.* 18: 251–256, 1995; Murren et al., A phase II trial of cyclosporin A in the treatment of refractory metastatic colorectal cancer, *Am. J. Clin. Oncol.* 14: 208–210, 1991). Hence, the identification of MDR-reversing drugs with low toxicity to the mammal or human undergoing chemotherapy is a major concern for the clinical treatment of MDR tumors.

Previously, macrocyclic lactone compounds such as the LL-F28249 compounds, the milbemycins and the avermectins have been widely used for treatment of nematode and arthropod parasites. The highly active LL-F28249 family of compounds are natural endectocidal agents isolated from the fermentation broth of *Streptomyces cyaneogriseus* subsp. *noncyanogenus*. U.S. Pat. No. 5,106,994 and its continuation U.S. Pat. No. 5,169,956 describe the preparation of the major and minor components, LL-F28249α-λ. The LL-F28249 family of compounds further includes, but is not limited to, the semisynthetic 23-oxo derivatives and 23-imino derivatives of LL-F28249α-λ which are shown in U.S. Pat. No. 4,916,154. Moxidectin, chemically known as 23-(O-methyloxime)-LL-F28249α, is a particularly potent 23-imino derivative. Other examples of LL-F28249 derivatives include, but are not limited to, 23-(semicarbazone)-LL-F28249α and 23-(thiosemicarbazone)-LL-F28249α.

The milbemycins, also known as the B-41 series of antibiotics, are naturally occurring macrocyclic lactones isolated from the microorganism, *Streptomyces hygroscopicus* subsp. *aureolacrimosus*. U.S. Pat. No. 3,950,360 shows the preparation of the macrolide antibiotics milbemycin$_{\alpha 1-\alpha 10}$, milbemycin$_{\beta 1-\beta 3}$ etc. These compounds are also commonly referred to as milbemycin A, milbemycin B, milbemycin D and the like, or antibiotic B-41A1, antibiotic B-41A3, etc.

The avermectins, also known as the C-076 family of compounds, are naturally occurring macrocyclic lactones produced by the soil actinomycete microorganism, *Streptomyces avermitilis*. U.S. Pat. No. 4,310,519 discloses the isolation and preparation of the major components $A_{1a}$ (e.cf avermectin $A_{1a}$), $A_{2a}$, $B_{1a}$ and $B_{2a}$, and the minor components $A_{1b}$ (e.c., avermectin $A_{1b}$), $A_{2b}$, $B_{1b}$ and $B_{2b}$. The C-076 family additionally embraces the semisynthetic derivatives such as the 22,23-dihydroavermectins described in U.S. Pat. No. 4,199,569. The semisynthetic derivatives include, but are not limited to, ivermectin, abamectin, doramectin, eprinomectin and the like.

Ivermectin (IVM), chemically known as 22,23-dihydroavermectin $B_1$ or 22,23-dihydro C-076 $B_1$, is shown, for example, to be an anthelmintic of great efficiency and low toxicity (Campbell, Ivermectin and Abamectin, Springer, N.Y., 1989). IVM has been successfully used orally, by subcutaneous injection or transdermal uptake to cure nematode infections in animals and has also been used in humans to treat several types of infections, such as onchocerciaisis (river blindness). Although the molecular mechanism of the antiparasitic effects of IVM is not completely understood, it is thought that IVM binds with high affinity to a glutamate-gated chloride channel in nematodes (Cully et al., Cloning of an avermectin-sensitive glutamate-gated chloride channel from *Caenorhabditis elegans, Nature* 371: 707–711, 1994). Indeed, IVM is highly selective for the invertebrate chloride channel but binds with only low affinity to the τ-aminobutyric acid-gated (GABA-gated) chloride channel in vertebrate brain (Cully et al., Solubilization and characterization of a high affinity ivermectin binding site from *Caenorhabditis elegans, Mol. Pharmacol.* 40: 326–332, 1991; Schaeffer et al., Avermectin binding in *Caenorhabditis elegans.* A two-state model for the avermectin binding site, *Biochem. Pharmacol.* 38: 2329–2338, 1989). The binding of IVM to the invertebrate glutamate-gated chloride channel, which is essentially irreversible, keeps the chloride channel open and prevents membrane depolarization, leading to the paralysis of the nematode. The low host toxicity of IVM is due to both the low affinity towards the host receptor and the compartmentalization of the receptor in the brain. IVM, which is very hydrophobic, does not effectively cross the blood-brain barrier at low concentrations (Chiu et al., Absorption, tissue distribution, and excression of tritium-labeled ivermectin in cattle, sheep and rat, *J. Agric. Food. Chem.* 38: 2072–2078, 1990).

In a study using transgenic mice that had their Pgp I function disrupted by homologous recombination, IVM accumulation in the brain and in several other organs was increased dramatically (Schinkel et al., Disruption of the mouse mdr1a P-glycoprotein gene leads to a deficiency in the blood-brain barrier and to increased sensitivity to drugs, *Cell* 77: 491–502, 1994). Ivermectin was observed as being toxic (CNS toxicity) in the mice with the knockout P-glycoprotein. The results led the authors of that study to postulate that the Pgp in normal tissues mediates IVM transport. However, no direct biochemical evidence was shown to support their conclusion. Furthermore, these workers did not demonstrate that ivermection was a multidrug resistance reversing agent. It has also been reported that ivermectin was actively transported across the membranes of canine kidney cells and that P-glycoprotein inhibitors such as verapamil and cyclosporin A inhibited this transport by these cells (Greenwald et al., "Mechanistic Studies of Passive and Active Transport Processes in MDCK Cells: Transport of Selected Anthelmintics," proceedings of the 41st Annual Meeting of the American Association of Veterinary Parasitologists, Jul. 20–23, 1996, Louisville, Ky.).

Additional studies involving ivermectin have shown acute neurotoxicity in normal mice pretreated with SDZ-PSC 833, a blocker of class I mdr gene-encoded Pgp which was developed for reversal of multidrug resistance of tumor cells (Didier et al., Decreased biotolerability for ivermectin and cyclosporin A in mice exposed to potent P-glycoprotein inhibitors, *Int. J. Cancer,* 63: 263–267, 1995). Recently, it has been suggested that ivermectin may act as a substrate and an inhibitor of Pgp but the study failed to adequately explain the ivermectin toxicity found in SDZ-PSC 833-treated mice (Didier et al., The abamectin derivative ivermectin is a potent P-glycoprotein inhibitor, *Anti-Cancer Drugs,* 7: 745–751, 1996).

BRIEF SUMMARY OF THE INVENTION

It is now found that the macrocyclic lactone endectocides are surprisingly powerful multidrug resistance reversing agents which are capable of enhancing the potency of certain chemotherapeutic agents against resistant tumors and other related cells. A new LL-F28249 derivative has also been found to unexpectedly possess potent multidrug resistance reversing properties which is useful for overcoming drug resistance in tumor cells and other diseases.

BRIEF DESCRIPTION OF THE DRAWINGS

The background of the invention and its departure from the art will be further described hereinbelow with reference to the accompanying drawings, wherein:

In FIG. 5A, drug-sensitive (CEM) and drug-resistant (CEM/VLB$^{1.0}$) cells are photoaffinity labelled with 20 nM [$^{125}$I]-

IAAP. Drug-sensitive (lane 1) and drug-resistant (lanes 2–14) cells are incubated in the absence (lanes 1–2) or the presence of a 1-fold (lanes 5, 8, 11 and 14), 10-fold (lanes 4, 7, 10 and 13) or 100-fold (lanes 3, 6, 9 and 12) molar excess of IVM (lanes 3–5), SDZ-PSC 833 (PSC 833; lanes 6–8), cyclosporin A (CsA; lanes 9–11) or verapamil (Vrp; lanes 12–14). FIG. 5B shows the percent inhibition of IAAP Pgp photolabelling from FIG. 5A as determined from densitometric scanning of Pgp photolabelled band. The signal in lane 2 (photolabelled Pgp in CEM/VLB$^{1.0}$ cells in the absence of drugs) is taken as control or 100%.

In FIG. 8A, drug-sensitive (CEM) and drug-resistant (CEM/VLB$^{1.0}$) cells are photoaffinity labelled with 20 nM [$^{125}$I]-IAAP. Cells are incubated in the absence (CEM/VLB$^{1.0}$) or presence of a 10-, 100- or 1000-fold molar excess of 23-(thiosemicarbazone)-LL-F28249α (CL182415), 23-(O-methyloxime)-5-(phenoxyacetoxy)-LL-F28249α (CL182168) and the isomeric mixture of (E) and (Z)-26-formyl-(O-methyloxime)-LL-F28249α, (CL182053). FIG. 8B shows the densitometric scanning analysis of the autoradiogram.

DETAILED DESCRIPTION OF THE INVENTION

Figure 1A:
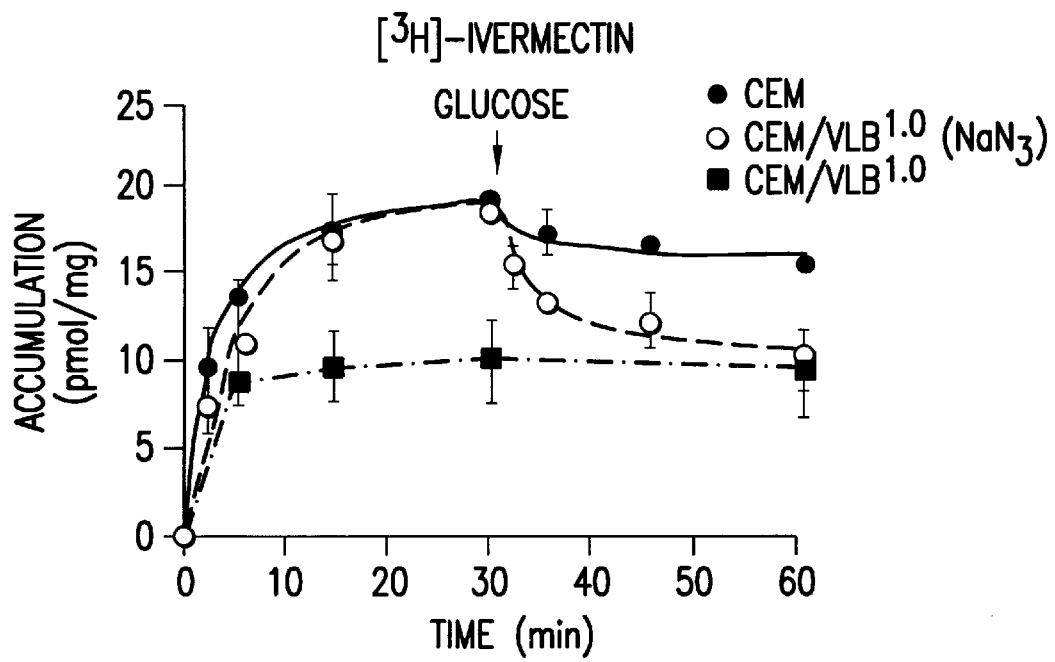
FIGS. 1A and 1B show ivermectin (IVM) and vinblastine (VLB) accumulation and efflux by cancer cells. Drug-sensitive (CEM) and drug-resistant (CEM/VLB$^{1.0}$) cells are incubated at 37° C. in α-MEM for 0–60 minutes in the presence 200 nM [$^3$H]-IVM (FIG. 1A) or [$^3$H]-vinblastine (FIG. 1B) alone or in the presence of 10 mM sodium azide. The cells are then washed and the efflux is carried out at 37° C. in α-MEM for times varying from 0–30 minutes. The accumulation values represent the mean±SD of three experiments.

In accordance with the present invention, there are provided novel methods for increasing the toxicity of certain chemotherapeutic agents against resistant tumor cells and other related cells which encompass the administration of multidrug resistant reversing agents to mammals suffering from cancer or related diseases. Surprisingly, the multidrug resistant reversing agents comprise macrocyclic lactone compounds.

Desirably, the macrocyclic lactone compounds for use in this invention are either isolated from Streptomyces, such as, for example, the LL-F28249 compounds, the milbemycins, the avermectins and the like or synthetically derived therefrom. Such macrocyclic lactones include, but are not limited to, the LL-F28249α-λ compounds, the 23-oxo or 23-imino derivatives thereof, the 22,23-dihydro derivatives of the avermectins and various milbemycin derivatives. Particularly desirable macrocyclic lactone compounds are LL-F28249α, 23-(O-methyloxime)-LL-F28249α, 23-(semicarbazone)-LL-F28249α, 23-(thiosemicarbazone)-LL-F28249α, the isomeric mixture of (E) and (Z)-26-formyl-(O-methyloxime)-LL-F28249α, ivermectin, abamectin, doramectin, eprinomectin, milbemycin A, milbemycin D and the biological equivalents thereof.

The chemotherapeutic agents may include, but are not limited to, the cytostatic hydrophobic chemotherapeutic drugs such as, for example, vinblastine, vincristine, doxorubicin, paclitaxel, colchicine, actinomycin D, gramicidin D and the like. It has been problematic in the use of these chemotherapeutic agents that resistant tumor cells have developed over the past few years. In particular, resistance has been observed in human lymphoma cells, human breast cancer cells, human ovarian cancer cells and human lung cancer cells. The present methods will be beneficial to combatting these and other similar cancerous tissues.

The compounds are administered to mammals orally, parenterally, topically (local activity) or transdermally (systemic activity) depending upon the bioavailability of the selected medicinal by the desired route of administration. Parenteral administration of medicinals encompasses any means other than orally, such as, for example, intravenously, intramuscularly, subcutaneously, intratracheally, intraruminally, etc. It is apparent that the MDR-reversing agents are administered in connection with the administration of the chemotherapeutic agents encountering resistance. However, the administration of the macrocyclic lactones may be made either before or during chemotherapy. If the MDR-reversing agent will be given before the chemotherapeutic drug, medical or veterinary personnel can readily determine from blood levels how far in advance the MDR-reversing agent may be given before chemotherapy for efficacy. Certainly, the selected dosage and the state of the disease (ecf non-metastatic or local versus metastatic or advanced degree of cancer) influences the timing of administration. Typically, the MDR-reversing agent will be administered within 24 hours of the onset of chemotherapy and, preferably, within 4 hours before or concomitantly with administering the chemotherapeutic drug. Due to a long half-life for many of the macrolides that varies between 1 and 8 days depending upon the species, the MDR-reversing agent may even be administered up to 8 days prior to the start of chemotherapy and still be effective for enhancing the potency of the chemotherapeutic agent.

In terms of dosage, the suitable amount of the macrocyclic lactone compounds which is effective to increase the toxicity of the chemotherapeutic agent against resistant tumors and other cells will typically vary within a wide range of amounts at a variety of concentrations. The nature or state of the disease and the selection of the chemotherapeutic agent will clearly affect the particular dose of the MDR-reversing agent. Under certain circumstances, the macrolides may be given, for instance, at the dosage of about 0.001 mg to about 10 mg per kg of body weight and preferably, about 1 mg to about 5 mg per kg of body weight. Other circumstances may warrant dosages either above or below this level. It is contemplated that selection of appropriate dosages of the chemotherapeutic agent and the multidrug resistant reversing agent to achieve the effective tumor suppressing amount can be easily titrated by routine testing known to those having ordinary skill in the medical and veterinary arts.

For use in chemotherapy treatment, the compounds of the present invention may be administered orally in a unit dosage form such as a capsule, bolus or tablet. The capsules and boluses comprise the active ingredient admixed with a conventional carrier vehicle such as starch, talc, magnesium stearate or dicalcium phosphate. The dry, solid unit dosage form are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be widely varied with respect to their total weight and content of the active agent depending upon factors such as the type and the weight of the mammal to be treated, the severity of the disease state and the type of tumor involved.

For animals, the active compound can be administered via an animal feedstuff by intimately dispersing the active ingredient in the feed or using it as a top dressing or in the form of pellets which may then be added to the finished feed or optionally fed separately. Suitable compositions include feed premixes or supplements in which the active compound is present in relatively large amounts, wherein said feed premixes or supplements are suitable for direct feeding to the animal or for addition to the feed either directly or after an intermediate dilution or blending step.

Typical carriers or diluents suitable for such compositions include distillers' dried grains, corn meal, citrus meal, fermentation residues, ground oyster shells, wheat products, molasses, corn cob meal, edible bean mill feed, soya grits, crushed limestone, etc. The compounds are intimately dispersed throughout the carrier by methods such as grinding, stirring, milling or tumbling. Compositions containing about 0.005% to about 2.0%, by weight, of the active compound are particularly suitable as feed premixes.

Feed supplements fed directly to the animal contain about 0.0002% to 0.3%, by weight, of the active compounds. Such supplements are added to animal feed in an amount to give the finished feed the concentration of active compound desired for treating the resistant tumor or other cancerous disease. Although the desired concentration of the compound will vary depending upon a variety of factors such as the particular compound employed or the severity of the disease state, the macrocyclic compounds of this invention are usually fed at concentrations of about 0.00001% to about 0.02% in the feed.

Alternatively, the active ingredients of the invention may be administered to the affected mammals parenterally. The macrocyclic compounds may be dissolved, dispersed or suspended in a sterile, isotonic, nontoxic liquid carrier vehicle. The compound is admixed with the nontoxic pharmaceutically acceptable vehicle, preferably a vegetable oil such as peanut oil, cotton seed oil or the like. Other parenteral vehicles such as propylene glycol, glycerol, etc. may also be used. A parenteral formulation comprising the macrolides and the chemotherapeutic agents may be lyophilized with optional excipients and reconstituted prior to administration using a suitable nontoxic pharmaceutically acceptable vehicle such as sterile saline, glucose in water, water, etc.

In the parenteral formulations, the active macrolides are typically dissolved or suspended in the formulation in sufficient amount to provide from about 0.005% to about 5.0%, by weight, of the active compound in said formulation.

Conveniently, the macrolides may also be administered to the affected mammals by the topical or transdermal route to achieve either local or systemic effect. For animals, the compounds may be applied as a liquid drench. The drench is normally a solution, suspension or dispersion of the active compound, usually in water, together with a suspending agent such as bentonite and a wetting agent or similar excipient. Generally, the drenches also contain an antifoaming agent. Drench formulations typically contain about 0.001% to about 0.5%, by weight, and preferably, about 0.01% to about 0.1%, by weight, of the active macrocyclic compound.

Additionally, the macrocyclic compounds and certain chemotherapeutic agents may be administered by applying as a gel, lotion, solution, cream or ointment to human skin or pouring on animal skin or hide via a solution. The topical or transdermal formulations comprise the active ingredient in combination with conventional inactive excipients and carriers. The cream, for example, may use liquid petrolatum, white petrolatum, propylene glycol, stearyl alcohol, cetyl alcohol, sodium lauryl sulfate, sodium phosphate buffer, polysorbates, parabens, emulsifying wax, polyoxyethylene-polyoxypropylene block copolymers, purified water and the like. Ointments, for example, may employ petrolatum, mineral oil, mineral wax, glycerin and the like. Topical solutions may provide the active ingredient compounded with propylene glycol, parabens, hydroxypropyl cellulose, preservatives. Pour-on formulations may constitute the active ingredient dissolved in a suitable inert solvent, such as dimethylsulfoxide, propylene glycol and the like. A particularly useful pour-on formulation comprises the active ingredient dissolved or dispersed in an aromatic solvent, PPG-2 myristyl ether propionate, polybutene, an antimicrobial agent, an antioxidant and a nontoxic pharmaceutically acceptable mineral or vegetable oil.

This invention deals with the unexpected findings that the macrocyclic lactone compounds such as moxidectin, a number of moxidectin analogues and ivermectin are potent P-glycoprotein binding drugs and that they can reverse multidrug resistance (MDR) in tumor and other cells. The results illustrate that IVM, for example, is a substrate for the Pgp drug efflux pump. Moreover, it is shown that IVM interacts with Pgp and surprisingly is a potent MDR-reversing agent. In view of their high affinity for P-glycoprotein, MDR-reversing property and inherent safety, the macrocyclic lactone compounds can play an important role in cancer therapy and other diseases in which MDR can be problematic. While some of the moxidectin analogues are shown to be marginally active as endectocides, they are surprisingly very potent MDR-reversing agents. This makes them useful as MDR-reversing agents either in cancer therapy or as reversing agents of endectocide resistance in nematodes and arthropods.

It is shown that IVM is a substrate for the Pgp drug efflux pump in human mdr cells. The results illustrate that [$^3$H]-IVM accumulates to a lesser extent in drug-resistant than in drug-sensitive cells. Moreover, the efflux studies show that [$^3$H]-IVM is effluxed rapidly from resistant cells and this transport is energy-dependent. These results are consistent with an earlier report which suggests that IVM may be a substrate for Pgp since the disruption of murine Pgp gene I from the mouse genome by homologous recombination leads to the accumulation of IVM in the brain and other tissues that intrinsically overexpress Pgp (Schinkel et al., Disruption of the mouse mdrla P-glycoprotein gene leads to a deficiency in the blood-brain barrier and to increased sensitivity to drugs, *Cell* 77: 491–502, 1994). Although the results of this and a previous study do support the contention that IVM is transported from mdr cells, IVM is less efficiently transported than [$^3$H]-vinblastine. It is not clear why these drugs are differentially transported from mdr cells. Such differences may be due to the high hydrophobicity of IVM as compared to that of vinblastine (octanol to water fractionation IVM/vinblastine=45). IVM is poorly soluble in aqueous solution. It has a tendency to partition in a hydrophobic environment offered by the cell membrane resulting in a low efflux. Furthermore, due to its higher affinity for Pgp, IVM can possess a slower dissociation constant than vinblastine ($K_D$ is 10.6 nM versus 400–500 nM for IVM and vinblastine, respectively) (Naito et al., ATP/Mg2+-dependent binding of vincristine to the plasma membrane of multidrug-resistant K562 cells, *J. Biol. Chem.* 263: 11887–11891, 1988; Cornwell et al., Certain calcium channel blockers bind specifically to multidrug-resistant human KB carcinoma membrane vesicles and inhibit drug binding to P-glycoprotein, *J. Biol. Chem.* 262: 2166–2170, 1987). The environmental chemistry results of moxidectin which are analogous to those of IVM, such as demonstrating a high hydrophobicity (n-octanol/water partition coefficient $K_{ow}$= 58,300) as well as a low solubility in water (0.51 mg/L), provide solid grounds for the MDR-reversing activity of moxidectin.

Earlier reports on the physical-chemical properties of various compounds that are thought to reverse the mdr phenotype (Nogae et al., Analysis of structural features of dihydropyridine analogs needed to reverse multidrug resistance and to inhibit photoaffinity labelling of P-glycoprotein, *Biochem. Pharmacol.* 38: 519–527, 1989; Pearce et al., Essential features of the P-glycoprotein pharmacophore as defined by a series of reserpine analogs that modulate multidrug resistance, *Proc. Natl. Acad. Sci. USA* 86: 5128–5132, 1989; Zamora et al., Physical-chemical properties shared by compounds that modulate multidrug resistance in human leukemic cells, *Molec. Pharmacol.* 33: 454–462, 1988) have indicated that lipophilicity as exemplified by one or more planar aromatic rings and a cationic charge are common to most MDR-reversing agents. Although these structural moieties are found in many MDR-reversing agents, their role in Pgp-drug binding and transport is presently unknown. Using nonionic detergents, which also reverse the mdr-phenotype at nontoxic concentrations, it has been previously demonstrated that hydrophobic interactions are likely to mediate Pgp drug binding, while the cationic charge associated with some lipophilic MDR-reversing agents may be important in drug transport (Zordan-Nudo et al., Effects of nonionic detergents on P-glycoprotein drug binding and reversal of multidrug resistance, *Cancer Res.* 53: 5994–6000, 1993). Currently, it is demonstrated that the octanol/water fractionation coefficient of IVM is 3- and 9-fold higher than that of cyclosporin A and verapamil, respectively. Moxidectin also demonstrates a significantly higher octanol/water fractionation coefficient ($K_{ow}$=58,300) than cyclosporin and verapamil. Hence, the observed differences in the reversing potential seen with the MDR-reversing agents with respect to their hydrophobicity are consistent with earlier findings (Zordan-Nudo et al., Effects of nonionic detergents on P-glycoprotein drug binding and reversal of multidrug resistance, *Cancer Res.* 53: 5994–6000, 1993; Nogae et al., Analysis of structural features of dihydropyridine analogs needed to reverse multidrug resistance and to inhibit photoaffinity labelling of P-glycoprotein, *Biochem. Pharmacol.* 38: 519–527, 1989; Pearce et al., Essential features of the P-glycoprotein pharmacophore as defined by a series of reserpine analogs that modulate multidrug resistance, *Proc. Natl. Acad. Sci. USA* 86: 5128–5132, 1989; Zamora et al., Physical-chemical properties shared by compounds that modulate multidrug resistance in human leukemic cells, *Molec. Pharmacol.* 33: 454–462, 1988).

The molecular mechanism by which Pgp mediates the efflux of drugs is presently not understood. However, using photoactive drug analogues, direct binding between Pgp and drugs has been extensively demonstrated (Nare et al., Characterization of rhodamine 123 binding to P-glycoprotein in human multidrug-resistant cells, *Molec. Pharmacol.* 45: 1145–1152, 1994; Foxwell et al., Identification of the multidrug resistance-related P-glycoprotein as a Cyclosporine binding protein, *Molec. Pharmacol.* 36: 543–546, 1989; Greenberger, Major photoaffinity drug labelling sites for iodoaryl-azidoprazosin in P-glycoprotein are within, or immediately C-terminal to, transmembrane domains 6 and 12, *J. Biol. Chem.* 268: 11471–11475, 1993). The results of the present invention show that IVM interacts directly with Pgp, since low molar excesses of IVM completely inhibits the photoaffinity labelling of Pgp with IAAP. Moreover, drugs (e.g. vinblastine or cyclosporin A) which interact with Pgp are shown to potentiate IVM accumulation in drug-resistant cells and to inhibit the binding of [$^3$H]-IVM to membranes from drug-resistant, but not from drug-sensitive cells. The failure of verapamil to inhibit [$^3$H]-IVM binding to plasma membranes is not clear. It may be speculated that IVM interacts with different sequences in Pgp than that of verapamil. Competitive inhibition of [$^3$H]-vinblastine and [$^3$H]-IVM binding to membranes from resistant cells shows that IVM completely inhibits [$^3$H]-VLB binding, while vinblastine only partially inhibits [$^3$H]-IVM binding. Cyclosporin A (CsA) is the only drug that totally inhibits IVM binding to Pgp. This suggests that these two drugs interact with similar binding sites. Interestingly, IVM is more efficient than SDZ-PSC 833 at inhibiting Pgp photo-affinity labelling with IAAP. The $IC_{50}$ for SDZ-PSC 833 is 1.2-fold lower than that of IVM for both VLB (vinblastine) and DOXO (doxorubicin); yet, it is also inherently more toxic to drug-sensitive and drug-resistant cells. Thus, it is likely that some of the MDR-reversal is due to SDZ-PSC 833 toxicity alone. By contrast, IVM is well-tolerated at plasma concentrations exceeding 680 ng/mL. In this invention, a 0.5 MM concentration or equivalent to a plasma concentration of 435 ng/mL is demonstrated as being sufficient to reverse 96% of the resistance in CEM/VLB$^{0.1}$ cells. Additionally, IVM possesses a long half-life that varies between 1 and 8 days according to species and the biological transformation rate is relatively slow (less than 50% after 14 days) (Chiu et al., Absorption, tissue distribution, and excression of tritium-labeled ivermectin in cattle, sheep and rat, *J. Agric. Food. Chem.* 38: 2072–2078, 1990). As a consequence, IVM has an unexpected advantage over SDZ-PSC 833 in reversing the mdr phenotype of tumors in clinical application.

The moxidectin series of compounds and ivermectin exemplify high P-glycoprotein binding affinity indicating that the macrocyclic lactone compounds can act as multi-drug resistance reversing agents. Furthermore, a number of the moxidectin analogues and ivermectin are very potent multidrug reversing agents and can have application in cancer treatment and other circumstances in which multi-drug resistance is problematic. These compounds can be used therapeutically in any mammal including animals or humans. While it is highly desirable to treat cancer affecting pets such as dogs, cats and horses, the compounds would find application in other farm or zoo animals as well. Moreover, their safety and multidrug resistance potency present real advantages for chemotherapy in humans compared with other multidrug resistance reversing agents which have significant side effects.

This invention further describes a new derivative of the LL-F28249 family of macrolides which has potent multi-drug resistance reversing properties. The novel isomeric mixture of (E) and (Z)-26-formyl-(o-methyloxime)-LL-F28249α has the following structure:

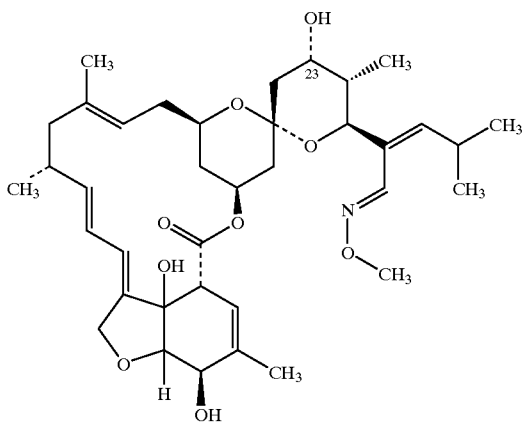

Generally, the isomeric mixture of (E) and (Z)-26-formyl-(O-methyloxime)-LL-F28249α may be prepared from LL-F28249α. First, an allylic bromide at the 27-position is prepared and converted to the 26-formyl derivative. This aldehyde is then reacted with methoxylamine hydrochloride to yield the aldehyde O-methyloxime. The reaction sequence is illustrated in greater detail as follows: As the starting material, LL-F28249α (30.3 g, 4.9 mmol) is dissolved in acetone (60 mL) and water (15 mL). The solution is immersed in an ice bath. N-Bromoacetamide (0.8558 g, 6.2 mmol) in acetone (60 mL) is added dropwise while the solution is under nitrogen, stirring. After the addition is complete, the solution is stirred an additional 45 minutes. Thereafter, the solution is diluted with $Et_2O$ (350 mL), washed with brine (50 mL), dried over magnesium sulfate and filtered to remove the solvent. The residue is flash chromatographed ($SiO_2$ using 1.5% isopropanol and $CH_2Cl_2$ as eluent before quenching).

To convert the allylic bromide to the aldehyde, the allylic bromide (0.234 g, 0.34 mmol) is dissolved in DMSO (4 mL) and $AgBF_4$ (73.5 mg, 1.1 eq, 0.38 mmol). The solution is stirred at room temperature under nitrogen for 7 hours. $Et_3N$ (100 μL) is added dropwise. After stirring an additional 15 minutes, the solution is diluted with 30 mL of water plus 20 mL of brine, and extracted twice with $Et_2O$ (30 mL each). Combined ethereal layers are then washed with water (10 mL), then brine (5 mL), dried over magnesium sulfate, filtered and the solvent is removed. The residue is flash chromatographed ($SiO_2$ using 2–3% isopropanol and $CH_2Cl_2$ as eluent) to yield 50 mg of the aldehyde product recovered from fractions 15–20 and identified by $^1HNMR$ and $^{13}CNMR$.

The aldehyde LL-F28249α product (41.0 mg, 65 μmol) is added to methoxylamine hydrochloride (40 mg, 470 μmol, 7 eq) and pyridine (0.1 mL) in ethanol (1 mL) and stirred under nitrogen at room temperature. After 17 hours reaction time, the mixture is diluted with toluene and then diluted with $Et_2O$ (6 mL), washed with water (1 mL), then brine, dried over magnesium sulfate, filtered and the solvent is removed. The residue is flash chromatographed ($SiO_2$ using 2% isopropanol and $CH_2Cl_2$ as eluent) to yield 29.8 mg of the final product, the isomeric mixture of (E) and (Z)-26-formyl-(O-methyloxime)-LL-F28249α, recovered from combining fractions 6–10 and identified by $^1HNMR$ and $^{13}CNMR$.

The following examples demonstrate certain aspects of the present invention. However, it is to be understood that these examples are for illustration only and do not purport to be wholly definitive as to conditions and scope of this invention. It should be appreciated that when typical reaction conditions (e.g., temperature, reaction times, etc.) have been given, the conditions which are both above and below these specified ranges can also be used, though generally less conveniently. The examples are conducted at room temperature (about 23° C. to about 28° C.) and at atmospheric pressure. All parts and percents referred to herein are on a weight basis and all temperatures are expressed in degrees centigrade unless otherwise specified.

A further understanding of the invention may be obtained from the following non-limiting examples.

EXAMPLES

Materials and Methods

For the materials which are used in the illustration of this invention, IVM and [$^3H$]-IVM are supplied by American Cyanamid Company (Princeton, N.J., USA). Cyclosporin A and its non-immunosuppressive analogue SDZ-PSC 833 are supplied by Sandoz Inc. (East Hanover, N.J.). Vinblastine is obtained from Aldrich Chemical Co. (Milwaukee, Wis.), verapamil and colchicine are from Sigma Chemical Co. (St. Louis, Mo.) and [$^{125}I$]-iodoaryl-azidoprazosin (2200 Ci/mmol) is purchased from DuPont New England Nuclear (Boston, Mass.). Drug-sensitive human lymphoma cells (CEM) (Beck, Vinca alkaloid-resistant phenotype in cultured human leukemic lymphoblasts, *Cancer Treat. Rep.* 67: 875–882, 1983) are supplied by St. Jude Children's Research Hospital (Memphis, Tenn.). The CEM/VLB$^{1.0}$ line is established from the CEM/VLB$^{0.1}$ line and is obtained from the B.C. Cancer Research Centre (Vancouver, B.C.). All other chemicals used are of the highest grade available.

Example 1

Tissue Culture and Plasma Membrane Preparation

CEM and CEM/VLB$^{1.0}$ cells are grown in α-minimal Eagle's Medium (MEM) by conventional methods (e.g., Beck, Vinca alkaloid-resistant phenotype in cultured human leukemic lymphoblasts, *Cancer Treat. Rep.* 67: 875–882, 1983). The CEM/VLB$^{1.0}$ cells are resistant to 1 μg/mL vinblastine and express high levels of Pgp compared to the sensitive cells (Zordan-Nudo et al., Effects of nonionic detergents on P-glycoprotein drug binding and reversal of multidrug resistance, *Cancer Res.* 53: 5994–6000, 1993). Plasma membranes are prepared using a calcium precipitation procedure essentially as described by Lin et al., *Biochemistry* 26: 731–736, 1987. Briefly, CEM and CEM/VLB$^{1.0}$ cells are washed three times in ice-cold phosphate buffered saline (PBS) and resuspended in a hypotonic lysis buffer (10 mM KCl, 1.5 mM $MgCl_2$, and 10 mM Tris-HCl, pH 7.4) containing protease inhibitors (2 mM phenylmethylsulfonyl fluoride, 30 μM leupeptin and pepstatin). Cells are homogenized using a Dounce glass homogenizer and the cell lysate is centrifuged at low speed (3000 g) to remove unbroken cells and nuclei. The resultant supernatant is made up to 10 mM $CaCl_2$ final concentration and mixed on ice. The calcium-induced membrane aggregates are precipitated by high speed centrifugation at 100,000 g for 1 hour at 4° C. using a Beckman SW50 rotor. The enriched plasma membrane pellet is washed with 10 mM Tris-HCl, pH 7.4, and 250 mM sucrose and stored at −80° C. until needed. The protein concentration is measured by the method of Bradford, A rapid and sensitive method for the quantitation of microgram quantities of protein utilizing the principle of protein-dye binding, *Anal. Biochem.* 72: 248–254, 1976.

Example 2

MTT Cytotoxicity Assay

Cells, cultured without drug for at least 1 week, are harvested in the exponential growth phase, and 100 μL aliquots are plated into 96-well plates at $0.5 \times 10^4$ for CEM and $1 \times 10^4$ for CEM/VLB per well. The cells are incubated for 24 hours at 37° C. before the addition of vinblastine plus/minus MDR-reversing agents. The cells are then cultured for 4 days and the MTT dye (3-(4,5-dimethylthiazol-2yl)-2,5-diphenyl tetrazolium bromide) is added to a final concentration of 0.5 mg/mL. The plates are incubated for 4 hours at 37° C. and the colored crystals formed from the tetrazolium salt are solubilized by the addition of 50 μL of 10% TRITON X-100® (a mixture of polyoxyethylene ethers commercially available from Sigma Chemical Company, St. Louis, Mo.) in 0.01N HCl and repetitively pipetted. The 96-well plates are heated in the microwave oven for 1 minute at the minimal power setting, and 10 μL of ethanol is added to disperse the bubbles formed during pipetting. Plates are read at 570 nM using an ELISA micro titer plate reader.

Example 3

Photoaffinity Labelling and SDS-PAGE

CEM and CEM/VLB$^{1.0}$ cells ($1 \times 10^6$) are washed 3 times in A-MEM and incubated in the dark for 30 minutes at 25° C. in the presence of 20 nM [$^{125}$I]-aryl-azidoprazosin (IAAP) with or without 1, 10, and 100-fold molar excess of IVM, SDZ-PSC 833, cyclosporin A, vinblastine or verapamil. The cells are set on ice for 10 minutes and irradiated with a 254 nm UV source (Stratagene UV crosslinker, Stratagene, La Jolla, Calif.). Cells are centrifuged at 500 g for 5 minutes, the supernatant removed and the pellet lysed in Tris-HCl pH 7.4 containing 5 MM MgCl$_2$ and 1% NP40. The proteins are resolved by SDS-polyacrylamide gel electrophoresis (SDS-PAGE) using the Fairbanks buffer system (Fairbanks et al., Electrophoretic analysis of major polypeptides of the human erythrocyte membrane, *Biochemistry* 10: 2606–2617, 1971). After electrophoresis, the gels are fixed in 40% methanol and 10% acetic acid for at least 1 hour. The gels are dried and exposed to a XAR Kodak film for 16 hours at −80° C.

Example 4

Drug Binding Assays

Plasma membranes from CEM and CEM/VLB$^{1.0}$ cells (20 μg) are preincubated in 10 mM Tris pH 7.4 containing 250 mM sucrose (TS) for 30 minutes at 37° C. in the presence of a 300-fold molar excess of unlabelled drugs (IVM, cyclosporin A, vinblastine, verapamil or colchicine). The cells are then incubated for 30 minutes at 37° C. in the presence of 20 nM [$^3$H]-IVM or vinblastine. The incubation is stopped with the addition of 1 mL of ice-cold TS. The membranes are washed twice with the same volume of TS and the membrane pellet is resuspended in 1 M NaOH and neutralized with the same volume of 1 M HCl 4 hours later. Drug binding is evaluated by liquid scintillation counting.

Example 5

Drug Transport

For drug accumulation, CEM and CEM/VLB$^{1.0}$ cells ($1 \times 10^6$) are washed 3 times in PBS containing 1 mg/mL glucose and preincubated for 30 minutes at 37° C. in the presence of 300-fold molar excess of unlabelled drugs (IVM, cyclosporin A, vinblastine, verapamil or colchicine). Cells are then incubated for 30 minutes at 37° C. in the presence of 0.2 μM [$^3$H]-IVM or [$^1$H]-vinblastine in a final volume of 100 μL. The incubation is stopped with the addition of 1 mL of ice-cold PBS containing 60 μM unlabelled IVM or vinblastine. Cells are then washed twice with the same stop solution and lysed in 100 μL of 1 M NaOH followed by neutralization with the same volume of 1 M HCl, 4 hours later.

For drug efflux, cells are preincubated for 30 minutes at 37° C. in the presence of 2 μM [$^3$H]-IVM or [$^3$H]-vinblastine and 10 mM sodium azide to inhibit drug efflux. Cells are washed and resuspended in PBS solution containing 1 mg/mL of glucose at 37° C. Samples are removed following 0–30 minute incubations. Cells are washed in 10 volumes of ice-cold PBS containing 2 μM of unlabelled drug. The final cell pellet is resuspended in 1 M NaOH followed by neutralization with the same volume of 1 M HCl, 4 hours later. The accumulation of labelled drugs is measured by liquid scintillation counting.

Example 6

Octanol Fractionation

Drugs are solubilized in octanol and mixed with an equal volume of PBS and strongly vortexed. After 30 minutes of agitation, the mixture is centrifuged at 1000 g for 5 minutes.

The upper (octanol) phase is separated from the lower (PBS) phase using a Pasteur pipette. The amount of drug in both phases is determined by measuring the UV absorbance. In some cases, after partitioning, the drugs are separated by high performance liquid chromatography (HPLC) to increase the sensitivity of the detection.

RESULTS

Ivermectin Transport in MDR Cells

Figure 1B:
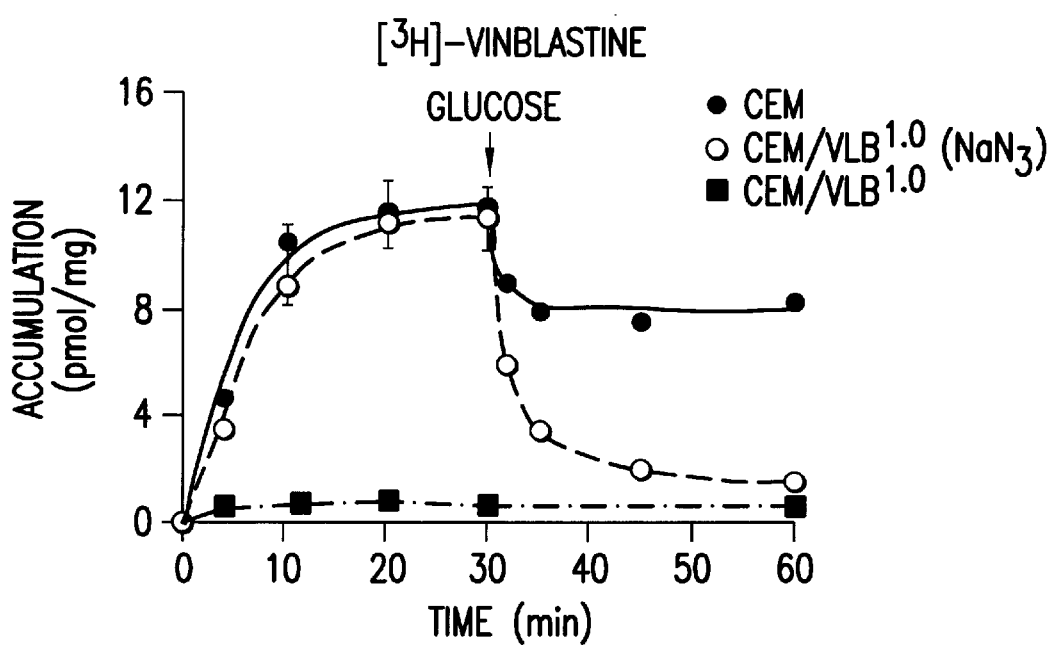

The demonstration that the disruption of Pgp class I gene in mice by homologous recombination results in IVM accumulation in the brain and other Pgp-positive tissues leads one to further experimentation and examination of the possibility of whether Pgp directly transports IVM. Here, FIGS. 1A and 1B show the accumulation and efflux of [$^3$H]-IVM or [$^3$H]-VLB in drug-sensitive (CEM) and drug-resistant (CEM/VLB$^{1.0}$) cells. [$^3$H]-IVM initial uptake and steady state accumulation are lower in CEM/VLB$^{1.0}$ than in CEM cells (FIG. 1A). Similar results are obtained with [$^3$H]-VLB, a known substrate of Pgp (FIG. 1B). The accumulation of [$^3$H]-IVM in resistant cells, is much higher than the accumulation [$^3$H]-VLB. Moreover, the results in FIGS. 1A and 1B show that the accumulation of [$^3$H]-VLB and [$^3$H]-IVM are energy-dependent since the addition of the metabolic inhibitor (10 mM sodium azide) to CEM/VLB$^{1.0}$ cells increases the accumulation of both drugs to the same level as that of CEM drug-sensitive cells. The results in FIGS. 1A and 1B also show the efflux of [$^3$H]-IVM and [$^3$H]-VLB from CEM and CEM/VLB$^{1.0}$ cells. The efflux of [$^3$H]-IVM from CEM/VLB$^{1.0}$ cells is much slower than that of [$^3$H]-VLB. Indeed, 40% of [$^3$H]-IVM remains in drug-resistant cells following 30 minutes of incubation. Taken together, these studies show that IVM is transported from drug-resistant cells in an energy-dependent manner.

Figure 2A:
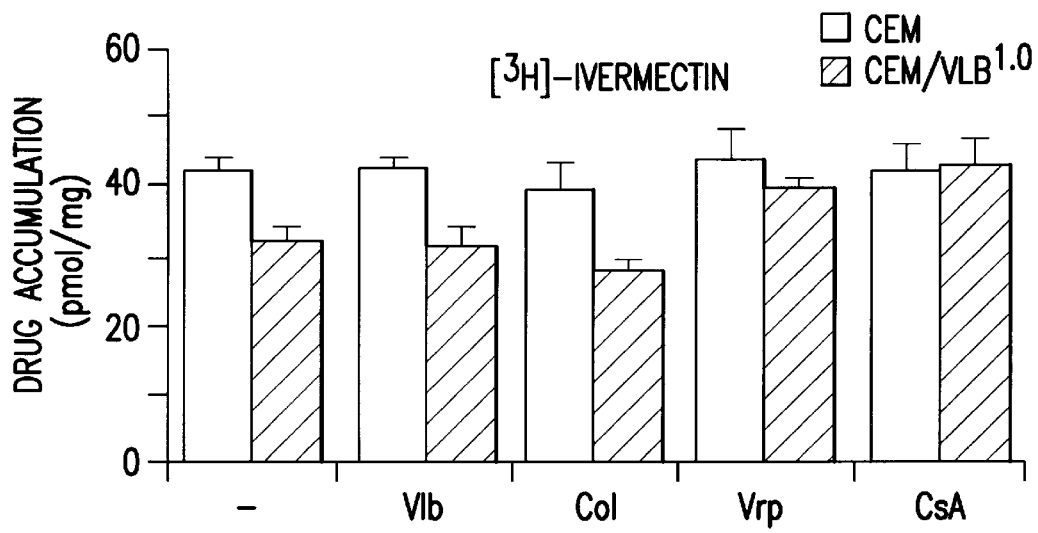
FIGS. 2A and 2B show the competitive inhibition of ivermectin and vinblastine uptake. Drug-sensitive (CEM) and drug-resistant (CEM/VLB$^{1.0}$) cells are incubated with 200 nM [$^3$H]-IVM (FIG. 2A) or [$^3$H]-vinblastine (FIG. 2B) in α-MEM for 30 minutes at 37° C. in the absence or presence of a 300-fold molar excess of ivermectin (Ivm), vinblastine (Vlb), colchicine (Col), verapamil (Vrp) or cyclosporin A (CsA). The accumulation values represents mean±SD of three experiments.
Figure 2B:
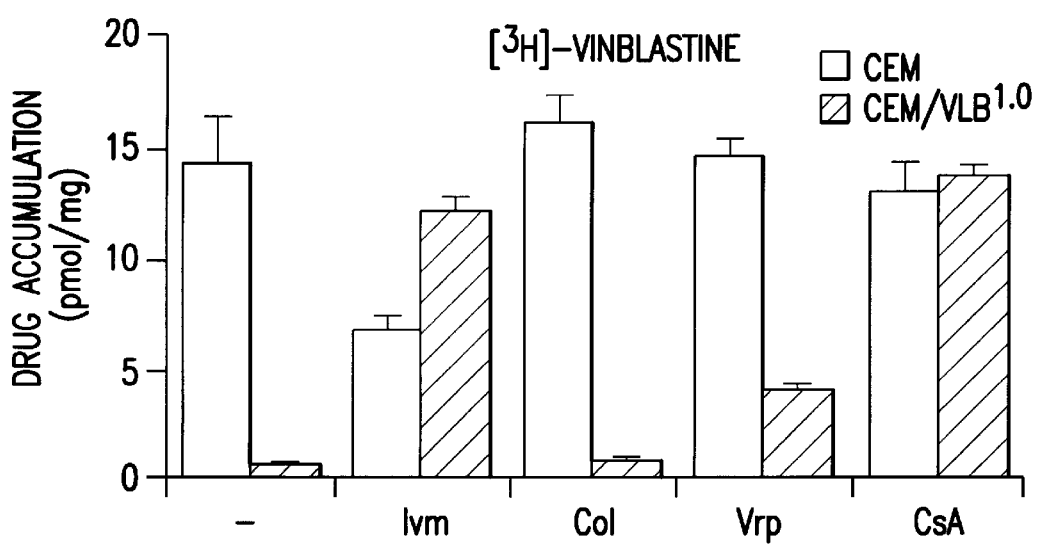

To determine if the accumulation of IVM in CEM/VLB cells is modulated by Pgp-associated drugs, [$^3$H]-IVM levels are measured in CEM and CEM/VLB$^{1.0}$ cells in the absence and in the presence of 300-fold molar excess of IVM, VLB, colchicine, verapamil, or cyclosporin A (FIG. 2A). FIG. 1A reveals higher levels of [$^3$H]-IVM accumulation in sensitive cells compared to resistant cells. However, the presence of unlabelled IVM, cyclosporin A or verapamil increases the accumulation of [$^3$H]-IVM to the same extent as that found in CEM cells, while vinblastine and colchicine are without effect (FIG. 2A). Similar results are also seen when [$^3$H]-VLB accumulation is measured in the presence of the above drugs. Both cyclosporin A and IVM at 300-fold excess completely restores the accumulation of [$^3$H]-VLB in CEM/VLB$^{1.0}$ cells (FIG. 2B). Interestingly, the presence of excess IVM results in a consistent decrease in [$^3$H]-VLB accumulation in sensitive cells (FIG. 2B). This decrease in [$^3$H]-VLB accumulation in CEM cells in the presence of IVM is not due to cell death since IVM is not toxic to cells for the duration of the experiment as determined by trypan blue staining.

Ivermectin Binding To Membranes From MDR Cells

Figure 3:
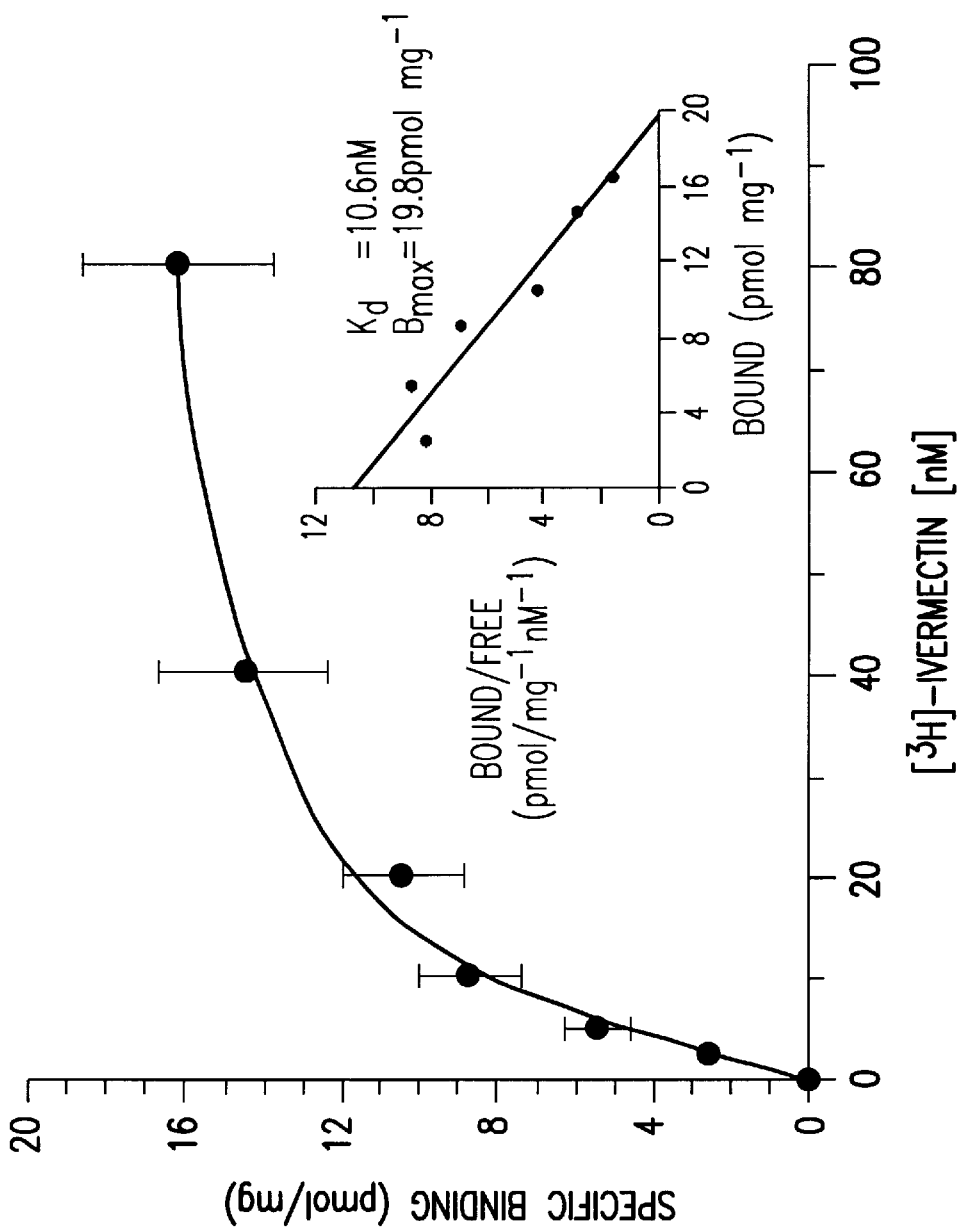
FIG. 3 shows the saturation binding of ivermectin to resistant cell plasma membranes. Plasma membranes (20 µg) are incubated with increasing concentrations (0–80 nM) of [$^3$H]-IVM. The nonspecific binding is half of total binding. A Scatchard plot is used to calculate the dissociation constant ($K_D$) and maximal binding value ($B_{max}$) Each value represents mean±S.E.M. from three experiments.
Figure 4A:
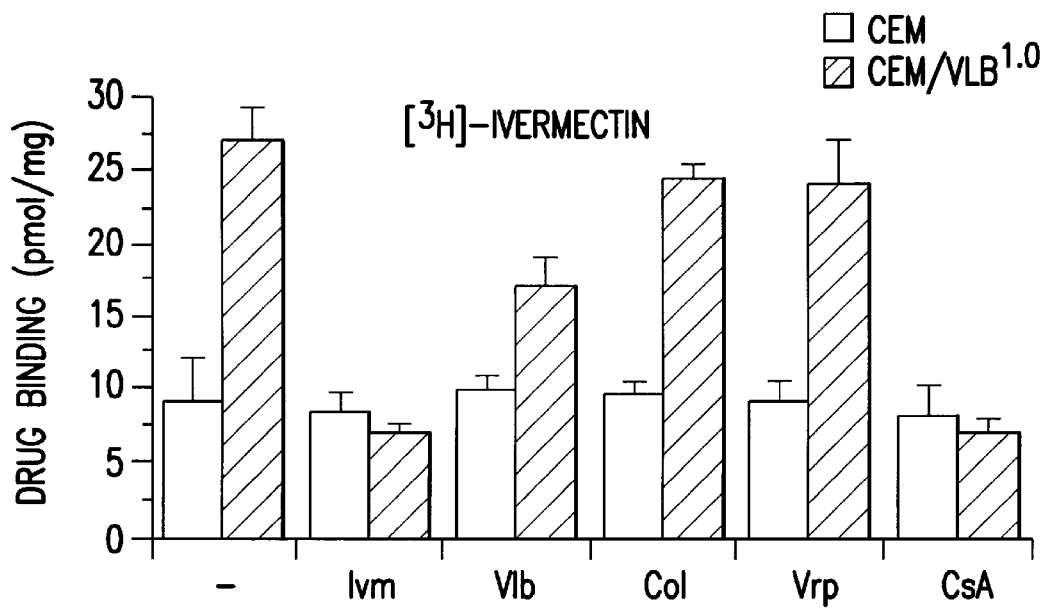
FIGS. 4A and 4B show the competitive inhibition of ivermectin and vinblastine binding to membranes from drug-sensitive and drug-resistant cells. Plasma membranes (20 µg) from CEM or CEM/VLB$^{1.0}$ cells are incubated with 20 nM [$^3$H]-IVM (FIG. 4A) or [$^3$H]-VLB (FIG. 4B) in the absence or presence of 300-fold molar excess of ivermectin (Ivm), vinblastine (Vlb), colchicine (Col), verapamil (Vrp) or cyclosporin A (CsA). The values for drug binding to membrane fractions are given as mean±SD of three experiments.
Figure 4B:
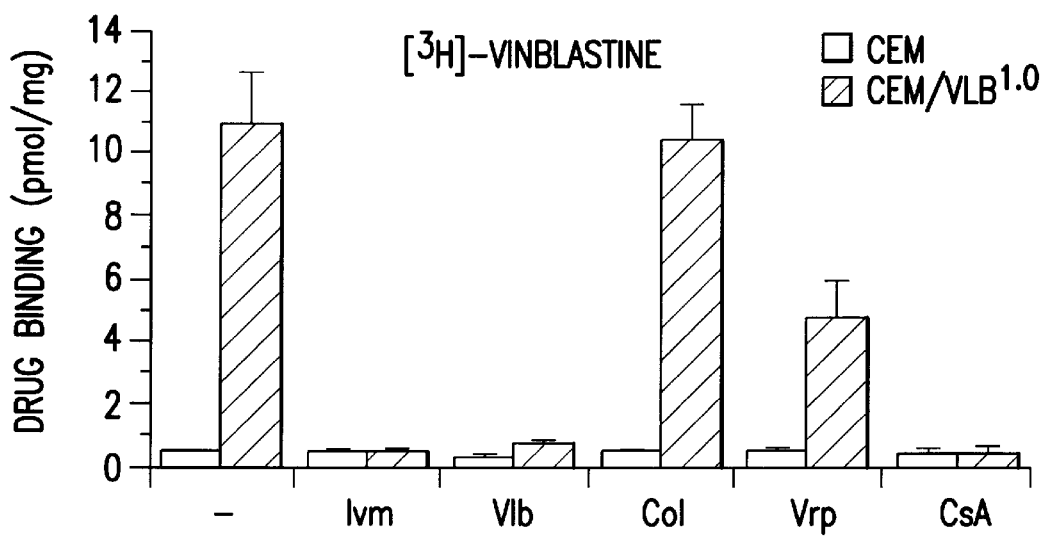

To determine if IVM interacts specifically and saturably with membranes from drug-resistant cell, the binding of [$^3$H]-IVM is measured over a large range of concentrations. The results in FIG. 3 show that IVM binding to membranes from CEM/VLB$^{1.0}$ is specific and saturable. The Scatchard transformation gives a single regression curve that yields an apparent $K_D$ of 10.6 nM and a $B_{max}$ value of 19.87 pmol/mg, respectively. To investigate further the nature of IVM interactions with MDR cells, [$^3$H]-IVM binding to membranes from CEM or CEM/VLB$^{1.0}$ in the absence and in the presence of drugs is measured and compared to that of [$^3$H]-VLB. FIGS. 4A and 4B show that [$^3$H]-IVM binds to a greater extent to membranes from CEM/VLB$^{1.0}$ than to CEM cell membranes. The presence of excess IVM and cyclosporin A completely inhibits [$^3$H]-IVM binding to CEM/VLB$^{1.0}$ membranes but has no effect on its binding to CEM membranes (FIG. 4A). Similarly, molar excess of vinblastine also inhibits [$^3$H]-IVM binding to CEM/VLB$^{1.0}$ membranes but to a lesser extend than unlabelled IVM or cyclosporin A. Interestingly, verapamil or colchicine has no effect on [$^3$H]-IVM binding. The results of [$^3$H]-VLB binding to membranes from CEM and CEM/VLB$^{1.0}$ in the absence and in the presence of drugs are similar to those obtained with [$^3$H]-IVM but with some differences. For example, although [$^3$H]-VLB binds more to CEM/VLB$^{1.0}$ than to CEM membranes, much less binding is seen with membranes from CEM cells (FIG. 4B). Moreover, verapamil but not colchicine also inhibits [$^3$H]-VLB binding to CEM/VLB$^{1.0}$ membranes (FIG. 4B). Taken together, these results show higher levels of [$^3$H]-IVM binding to membranes from resistant cells and that this binding is inhibited by drugs that interact directly with Pgp.

Inhibition of Pqp Photoaffinity Labelling

Figure 5A:
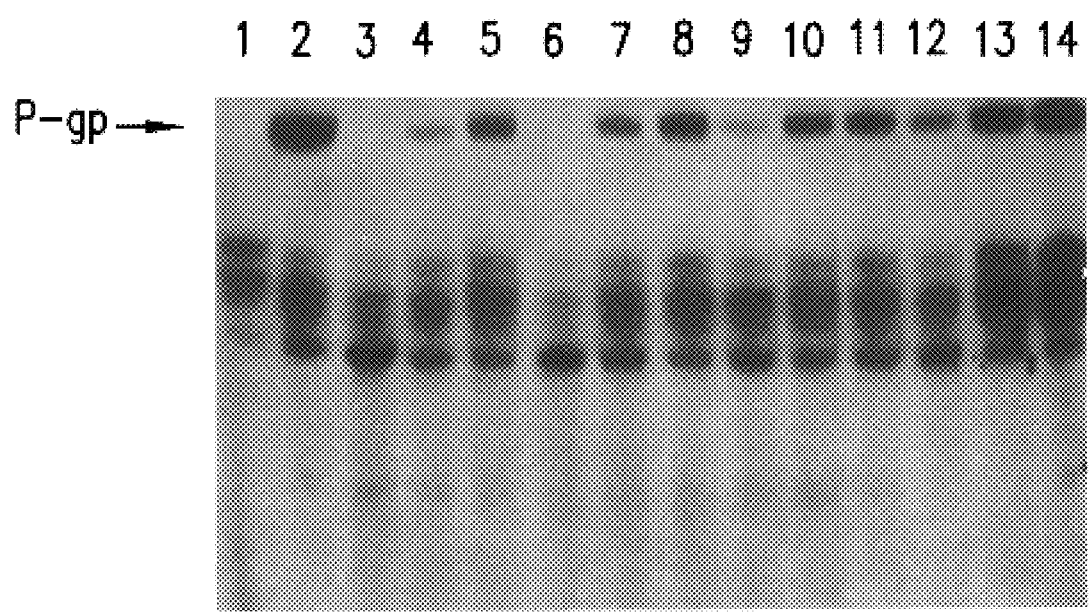
FIGS. 5A and 5B show the competitive inhibition of iodoaryl-azidoprazosin (IAAP) photoaffinity labelling.
Figure 5B:
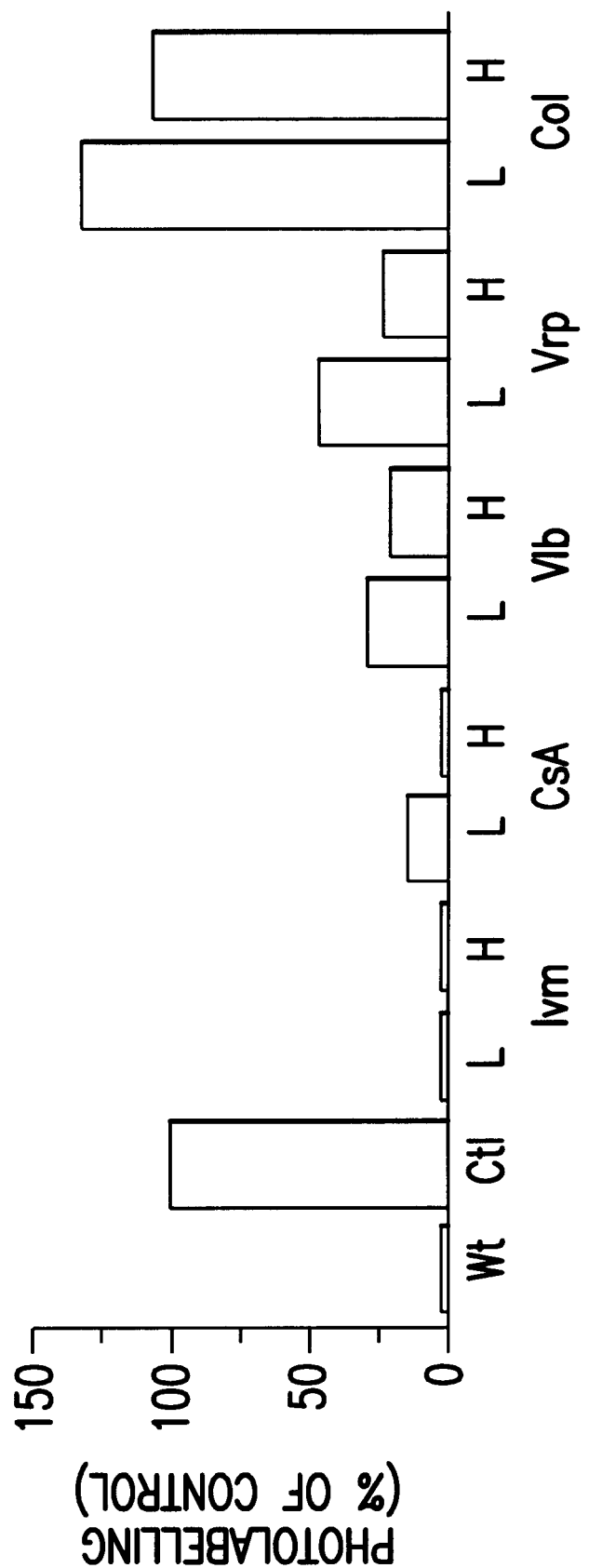

The $\alpha_1$-adrenergic receptor ligand, iodoarylazidoprazosin (IAAP), has previously been shown to specifically photolabel Pgp (Greenberger et al., Photoaffinity probes for the α1-adrenergic receptor and the calcium channel bind to a common domain in P-glycoprotein, *J. Biol. Chem.* 265: 4394–4401, 1990). It has also been suggested that drugs that inhibit photoaffinity labelling of Pgp by IAAP are likely to interact directly with Pgp and compete for its drug binding site(s) (Pearce et al., Essential features of the P-glycoprotein pharmacophore as defined by a series of reserpine analogs that modulate multidrug resistance, *Proc. Natl. Acad. Sci. USA* 86: 5128–5132, 1989). Thus, to determine if IVM interacts directly with Pgp, membranes from CEM or CEM/VLB$^{1.0}$ cells are photolabelled with 20 nM IAAP in the presence of 1-, 10- and 100-fold molar excess of IVM and other Pgp-associated drugs (FIGS. 5A and 5B). The results in FIG. 5A show a 170 kDa photolabelled protein in membranes from resistant but not from drug-sensitive cells (lanes 2 and 1, respectively). The presence of 100-fold excess of IVM, and SDZ-PSC 833 completely inhibits the photolabelling of Pgp with IAAP (lanes 3 and 6). Similar molar excess of cyclosporin A or verapamil are less effective (lanes 9 and 12). Interestingly, IVM at 10-fold molar excess is more effective than SDZ-PSC 833 in inhibiting the photolabelling of Pgp with IAAP (lanes 4 and 7).

Figure 6A:
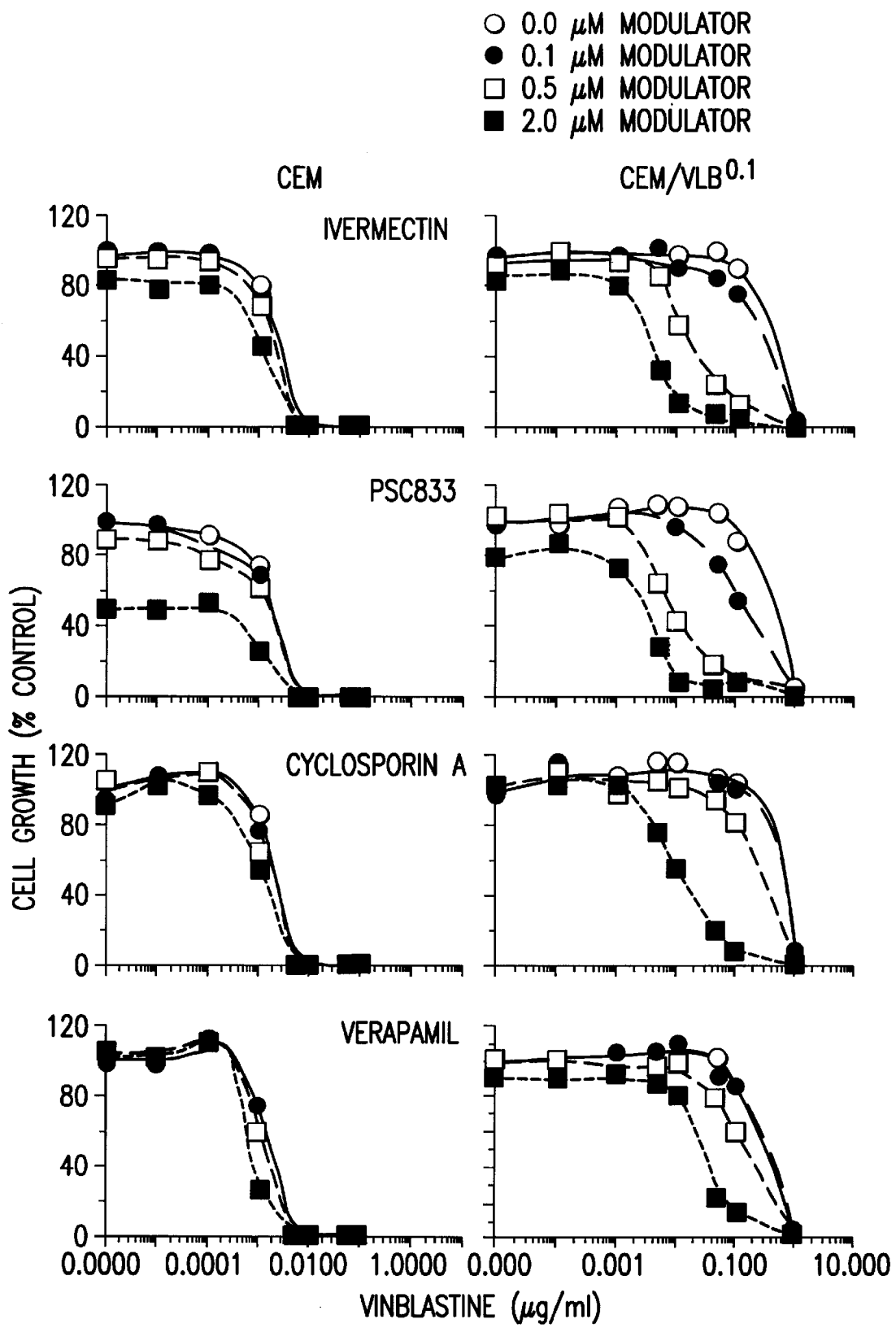
FIGS. 6A and 6B show the modulation of vinblastine resistance (FIG. 6A) and doxorubicin resistance (FIG. 6B) by ivermectin, SDZ-PSC 833 (PSC 833), cyclosporin A and verapamil. Drug-sensitive (CEM; 0.5×10$^4$) and drug-resistant (CEM/VLB$^{0.1}$; 1×10$^4$) cells are plated and incubated for 24 hours. Vinblastine or doxorubicin is then added (0–5 Mg/mL or 0–10 g/mL, respectively) in the absence and in the presence of IVM, SDZ-PSC 833 (PSC 833), cyclosporin A, or verapamil (0.1, 0.5 or 2 $\mu$M). After a 96-hour exposure, the viability of CEM and CEM/VLB$^{0.1}$ are estimated by measuring the absorbance at 450 nm. Each point is the mean (±SD) of three independent experiments.
Figure 6B:
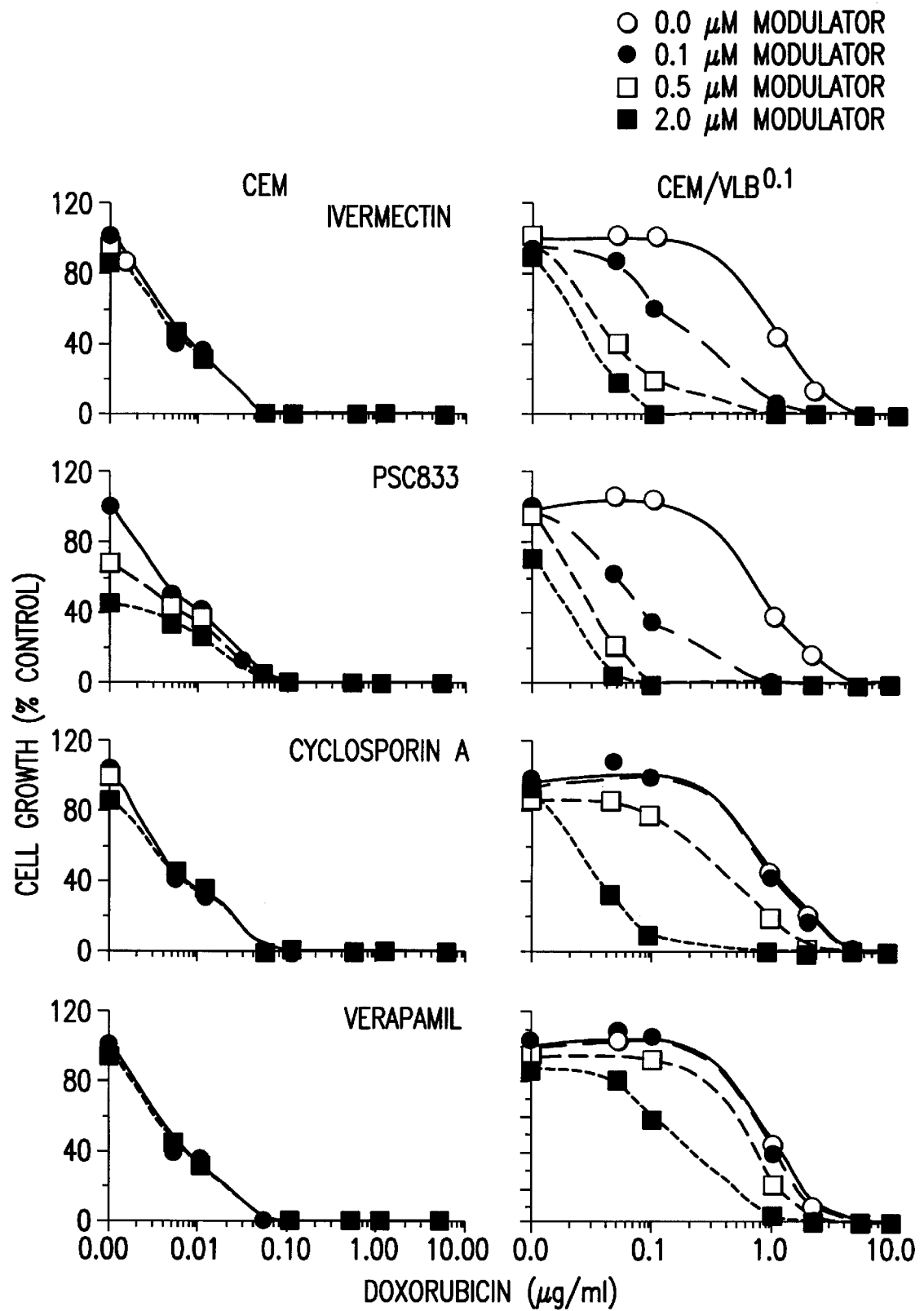

Reversal of MDR With Ivermectin Given the above results and the low host toxicity of IVM, it is then determined if IVM potentiates the toxicity of vinblastine or doxorubicin (DOXO) in highly drug-resistant human lymphoma cells. Therefore, CEM or CEM/VLB$^{0.1}$ cells are incubated with increasing concentrations of vinblastine or doxorubicin in the absence or in the presence of IVM, SDZ-PSC 833, cyclosporin A or verapamil (0, 0.1, 0.5 or 2 $\mu$M). The potentiation of drug toxicity by IVM and other MDR-reversing agents is determined by the MTT cytotoxicity assay (FIGS. 6A and 6B). The IC$_{50}$ values for vinblastine or doxorubicin for CEM and CEM/VLB$^{0.1}$ are 3.5 ng/mL and 500 ng/mL or 25 ng/mL and 1100 ng/mL, respectively. The presence of IVM, cyclosporin A, and verapamil alone has no significant effect on the viability of CEM or CEM/VLB$^{0.1}$ cells (FIGS. 6A and 6B). SDZ-PSC 833, a potent MDR-reversing agent (Watanabe et al., Comparative study on reversal efficacy of SDZ-PSC 833, cyclosporin A and verapamil on multidrug resistance in vitro and in vivo, *Acta Oncol.* 34: 235–241, 1995), at 2 $\mu$M is toxic to both CEM and CEM/VLB$^{0.1}$ cells (FIGS. 6A and 6B). Table 1 shows the IC$_{50}$ of CEM/VLB$^{0.1}$ cells to vinblastine or doxorubicin in the presence of increasing concentrations of IVM, SDZ-PSC 833, cyclosporin A and verapamil. A comparison between IVM and the other MDR-reversing agents (e.g., verapamil, cyclosporin A, and SDZ-PSC 833) shows that IVM at 2 $\mu$M is approximately 9-fold and approximately 4-fold better than verapamil and cyclosporin A in potentiating the toxicity of vinblastine or doxorubicin (FIG. 6A, FIG. 6B and Table 1). SDZ-PSC 833 is approximately 1.2-fold better than IVM in potentiating the toxicity of vinblastine or doxorubicin. However, SDZ-PSC 833 alone is much more toxic to CEM and CEM/VLB$^{0.1}$ cells (FIGS. 6A and 6B).

TABLE 1

Modulation of Resistance to Vinblastine and Doxorubicin by Different Reversing Agents

| Reversing Agent | Concentration ($\mu$M) | IC$_{50}$* (ng/mL) | Modulation ratio† |
|---|---|---|---|
| Vinblastine alone | | 500.0 ± 22.0 | |
| Ivermectin | 0.1 | 310.0 ± 17.0 | 1.6 ± 0.09 |
| | 0.5 | 16.0 ± 1.1 | 31.2 ± 2.15 |
| | 2.0 | 3.4 ± 0.6 | 147.0 ± 25.90 |
| SDZ-PSC 833 | 0.1 | 165.0 ± 12.0 | 3.0 ± 0.22 |
| | 0.5 | 9.0 ± 0.7 | 55.0 ± 4.28 |
| | 2.0 | 2.8 ± 0.1 | 178.0 ± 6.35 |
| Cyclosporin A | 0.1 | 500.0 ± 16.0 | N.A. |
| | 0.5 | 300.0 ± 14.0 | 1.7 ± 0.08 |
| | 2.0 | 13.0 ± 0.9 | 38.5 ± 2.67 |

TABLE 1-continued

Modulation of Resistance to Vinblastine
and Doxorubicin by Different Reversing Agents

| Reversing Agent | Concentration (µM) | IC$_{50}$* (ng/mL) | Modulation ratio† |
|---|---|---|---|
| Verapamil | 0.1 | 500.0 ± 16.0 | N.A. |
|  | 0.5 | 350.0 ± 16.0 | 1.4 ± 0.06 |
|  | 2.0 | 30.0 ± 2.2 | 16.7 ± 1.22 |
| Doxorubicin alone |  | 1100.0 ± 43.0 |  |
| Ivermectin | 0.1 | 164.0 ± 5.0 | 6.7 ± 0.20 |
|  | 0.5 | 34.0 ± 1.5 | 32.4 ± 1.43 |
|  | 2.0 | 24.0 ± 2.0 | 45.8 ± 3.84 |
| SDZ-PSC 833 | 0.1 | 80.0 ± 3.6 | 13.8 ± 0.62 |
|  | 0.5 | 29.0 ± 2.1 | 38.0 ± 2.75 |
|  | 2.0 | 18.0 ± 1.2 | 61.1 ± 4.07 |
| Cyclosporin A | 0.1 | 930.0 ± 41.0 | 1.2 ± 0.05 |
|  | 0.5 | 410.0 ± 19.0 | 2.7 ± 0.12 |
|  | 2.0 | 35.0 ± 1.5 | 31.0 ± 1.33 |
| Verapamil | 0.1 | 1000.0 ± 58.0 | 1.1 ± 0.06 |
|  | 0.5 | 664.0 ± 43.0 | 1.7 ± 0.11 |
|  | 2.0 | 153.0 ± 11.0 | 7.2 ± 0.52 |

*An IC$_{50}$ drug concentration is obtained from FIGS. 6A and 6B and represents 50% inhibition of MTT dye formation. Each value is the mean ± SD (standard deviation) of at least three determinations.
†The modulation ratio is calculated from the IC$_{50}$ for drug alone (vinblastine or doxorubicin) versus the IC$_{50}$ in the presence of the modulating agent. N.A. = not applicable.

Relative Hydrophobicity of Ivermectin

To further analyze the effect of IVM as an MDR-reversing agent, the hydrophobicity of IVM is evaluated using octanol/water fractionation coefficient and compared to other Pgp-associated drugs or MDR-reversing agents. The results in Table 2 show the octanol/water fractionation coefficients for colchicine, vinblastine, verapamil, cyclosporin A and IVM, to be 14, 30, 145, 518 and 1358, respectively. When the latter coefficients are compared with respect to the ability of drugs to inhibit binding, transport, or reverse the MDR of CEM/VLB$^{1.0}$ cells (Table 2), a strong correlation between hydrophobicity and these parameters can be observed. However, some exceptions are observed. For example, verapamil which is more hydrophobic than vinblastine, is a better inhibitor of drug transport, although photolabelling and binding are preferentially inhibited by vinblastine.

Moxidectin and Moxidectin Analogs as MDR-Reversing Agents

In addition to the above example of the avermectin, ivermectin as a multidrug reversing agent, other examples of macrocyclic lactone compounds, such as moxidectin and various moxidectin analogs, as multidrug resistance reversing agents are illustrated herein.

Figure 7:
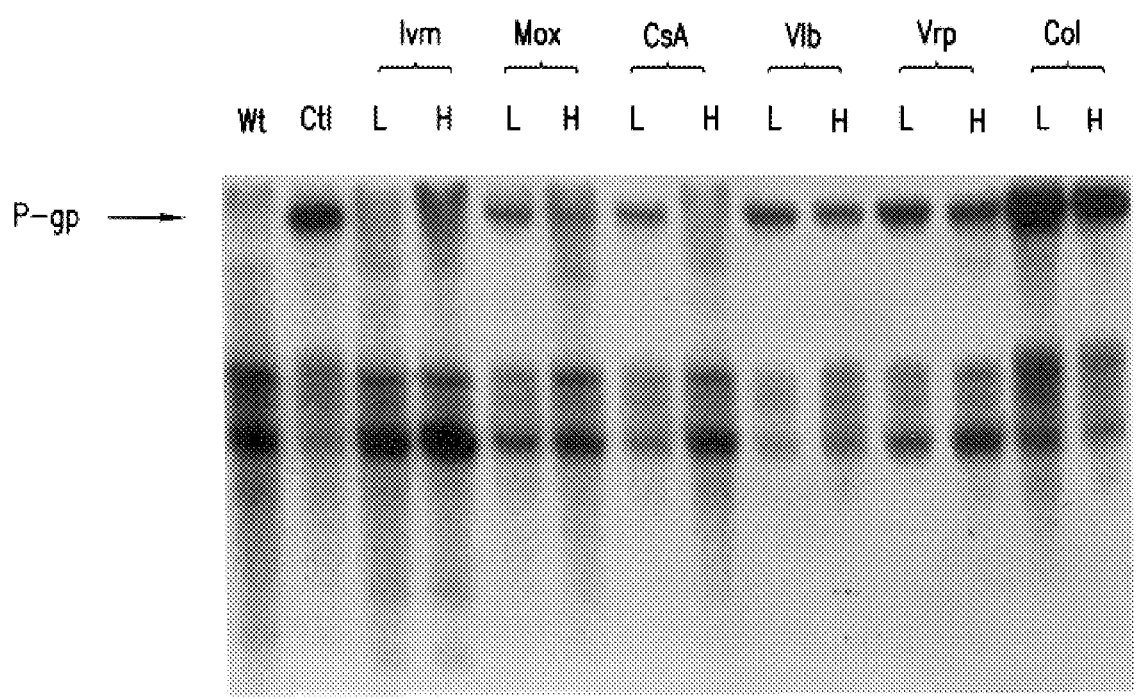
FIG. 7 shows the competitive inhibition of iodoaryl-azidoprazosin photoaffinity labelling. Drug-sensitive (CEM) and drug-resistant (CEM/VLB$^{1.0}$) cells are photoaffinity labelled with 20 nM [$^{125}$I]-IAAP. Drug-sensitive (Wt) and drug-resistant cells are incubated in the absence (Ctl) or presence of 200-fold (L) or 1000-fold (H) molar excess of ivermectin (Ivm), moxidectin (Mox), cyclosporin A (CsA), vinblastine (Vlb), verapamil (Vrp) and colchicine (Col).

The interaction of moxidectin with P-glycoprotein is compared with that of a variety of other P-glycoprotein binding drugs and a drug which does not bind to P-glycoprotein (colchicine). These experiments are performed using [$^{125}$I]-aryl-azidoprazosin (IAAP) photoaffinity labelling. While moxidectin has the ability to displace IAAP photoaffinity labelling of P-glycoprotein as compared to the control, it is found that ivermectin more strongly displaces IAAP photoaffinity labelling of P-glycoprotein than does moxidectin (FIG. 7).

Figure 8A:
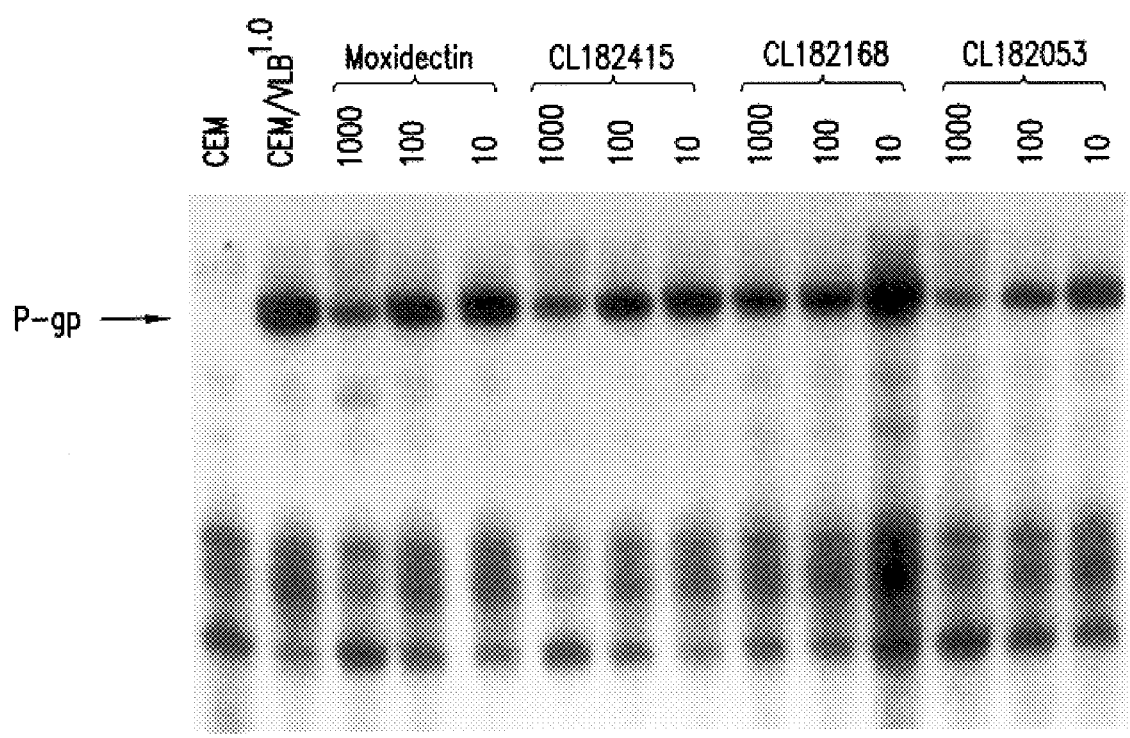
FIGS. 8A and 8B show the competitive inhibition of iodoaryl-azidoprazosin photoaffinity labelling by different moxidectin analogues.
Figure 8B:
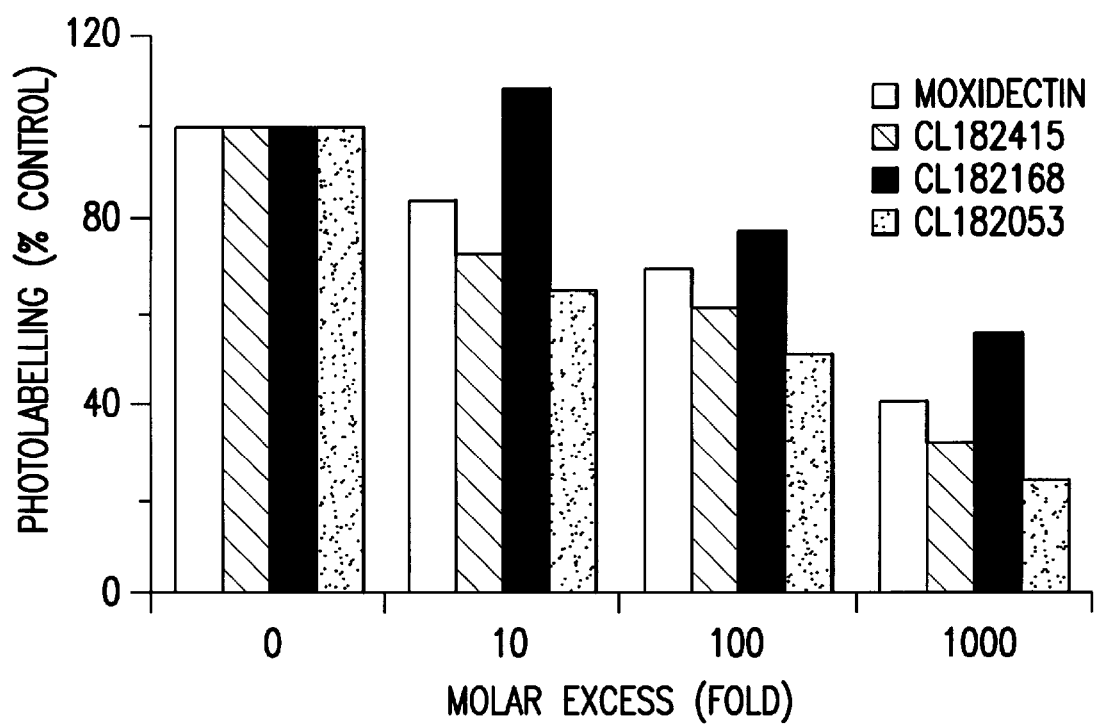

Several moxidectin derivatives are also assessed for their ability to displace IAAP photoaffinity labelling. The ability to block azidoprazosin binding of P-glycoprotein evidences their likely activity as multidrug resistance reversing agents. Photolabelling experiments are performed with 5 different analogues of moxidectin (FIGS. 8A and 8B). The moxidectin analogues appear to possess a strong affinity for P-glycoprotein and to be good MDR-reversing agents. All the moxidectin analogues tested are highly hydrophobic, and are found to interact with P-glycoprotein. With the exception of 23-(O-methyloxime)-5-(phenoxyacetoxy)-LL-F28249α, all are more effective in displacing IAAP than moxidectin. This compound, 23-(O-methyloxime)-5-(phenoxyacetoxy)-LL-F28249α, possesses a benzene ring which appears to present a size limitation for P-glycoprotein binding. While a high affinity for P-glycoprotein may be useful for reversing multidrug resistance in cancer cells, a low affinity for P-glycoprotein may be desirable in other cells if the resistance is associated with P-glycoprotein driven efflux from the cell.

Both charged analogues 23-(thiosemicarbazone)-LL-F28249α and 23-(semicarbazone)-LL-F28249α are found to be better inhibitors of IAAP photolabelling than moxidectin, showing a 15 to 20% higher displacement compared to moxidectin at the inhibitor level of a 1000-fold molar excess. An excellent photolabelling inhibitor is the isomeric mixture of (E) and (Z)-26-formyl-(O-methyloxime)-LL-

TABLE 2

Effect of MDR-Reversing Agents on Resistant (CEM/VLB$^{1.0}$) Cells

| Drugs | Octanol (F.C.) | IAAP photo-labelling (% of control)† | VLB binding (% of control)‡ | IVM binding (% of control)‡ | VLB transport (% of control)‡ | IVM transport (% of control)‡ | Increase in VLB sensitivity¥ (drgus at 2 µM) |
|---|---|---|---|---|---|---|---|
| IVM | 1358 ± 157 | 0 ± 0 | 0 ± 0 | 0 ± 0 | 13 ± 4 | 2 ± 1 | 147.2x |
| CsA | 518 ± 28 | 5 ± 0 | 0 ± 0 | 0 ± 0 | 4 ± 2 | 0 ± 0 | 38.5x |
| Verapamil | 154 ± 11 | 25 ± 7 | 42 ± 7 | 84 ± 12 | 71 ± 11 | 22 ± 7 | 16.7x |
| VLB | 30 ± 5 | 13 ± 5 | 4 ± 1 | 44 ± 15 | 96 ± 7 | 100 ± 13 | N.A. |
| Colchicine | 14 ± 2 | 102 ± 6 | 95 ± 4 | 86 ± 9 | 93 ± 9 | 100 ± 14 | N.D. |

Each value is the mean ± SD (standard deviation) of at least three determinations.
F.C. = fractionation coefficient (octanol phase/water phase).
†, ‡ Competition at 100x(†) and 300x(‡) molar excess.
¥ Increase in sensitivity = IC$_{50}$ in the absence of reversing agent/IC$_{50}$ in the presence of reversing agent. N.A. = not applicable. N.D. = not determined.

F28249α, which shows a 30% to 40% increase in displacement, compared with moxidectin, at an inhibitor concentration of 1000-fold molar excess. The results indicate that this molecule possesses powerful multidrug resistance reversing properties.

In the foregoing, there has been provided a detailed description of particular embodiments of the present invention for the purpose of illustration, and not limitation. It is to be understood that all other modifications, ramifications and equivalents obvious to those having skill in the art based on this disclosure are intended to be included within the scope of the invention as claimed.

We claim:

1. A method for increasing the toxicity of a cytostatic hydrophobic chemotherapeutic agent against a resistant tumor cell in a mammal which comprises administering a multidrug resistant reversing agent to the mammal in connection with administering the cytostatic hydrophobic chemotherapeutic agent in an amount effective to increase the toxicity of the chemotherapeutic agent, wherein the multidrug resistant reversing agent is a macrocyclic lactone compound selected from the group consisting of LL-F28249α-λ, a 23-oxo derivative of LL-F28249α-λ, a 23-imino derivative of LL-F28249α-λ, an avermectin, a 22,23-dihydro derivative of avermectin and a milbemycin.

2. The method according to claim 1, wherein the macrocyclic lactone compound is administered orally, parenterally, topically or transdermally.

3. The method according to claim 1, wherein the macrocyclic lactone compound is LL-F28249α, 23-(O-methyloxime)-LL-F28249α, 23-(semicarbazone)-LL-F28249α, 23-(thiosemicarbazone)-LL-F28249α, an isomeric mixture of (E) and (Z)-26-formyl-(O-methyloxime)-LL-F28249α, ivermectin, abamectin, doramectin, eprinomectin, milbemycin A or milbemycin D.

4. The method according to claim 1, wherein the chemotherapeutic agent is selected from the group consisting of vinblastine, vincristine, doxorubicin, paclitaxel, colchicine, actinomycin D and gramicidin D.

5. The method according to claim 1, wherein the mammal is selected from the group consisting of a human, a dog, a cat and a horse.

6. The method according to claim 1, wherein the resistant tumor cell is selected from the group consisting of a human lymphoma cell, a human breast cancer cell, a human ovarian cancer cell and a human lung cancer cell.

7. An improved method for treating a resistant tumor cell in a mammal which comprises administering to the mammal a tumor suppressing amount of a cytostatic hydrophobic chemotherapeutic agent and a multidrug resistant reversing agent, wherein the multidrug resistant reversing agent is a macrocyclic lactone compound selected from the group consisting of LL-F28249α-λ, a 23-oxo derivative of LL-F28249α-λ, a 23-imino derivative of LL-F28249α-λ, an avermectin, a 22,23-dihydro derivative of avermectin and a milbemycin.

8. The method according to claim 2, wherein the macrocyclic lactone compound is administered before or concomitantly with the chemotherapeutic agent.

9. The method according to claim 7, wherein the macrocyclic lactone compound is administered orally, parenterally, topically or transdermally.

10. The method according to claim 7, wherein the macrocyclic lactone compound is LL-F28249α, 23-(O-methyloxime)-LL-F28249α, 23-(semicarbazone)-LL-F28249α, 23-(thiosemicarbazone)-LL-F28249α, an isomeric mixture of (E) and (Z)-26-formyl-(O-methyloxime)-LL-F28249α, ivermectin, doramectin, eprinomectin, milbemycin A or milbemycin D.

11. The method according to claim 7, wherein the chemotherapeutic agent is selected from the group consisting of vinblastine, vincristine, doxorubicin, paclitaxel, colchicine, actinomycin D and gramicidin D.

12. The method according to claim 7, wherein the mammal is selected from the group consisting of a human, a dog, a cat and a horse.

13. The method according to claim 7, wherein the resistant tumor cell is selected from the group consisting of a human lymphoma cell, a human breast cancer cell, a human ovarian cancer cell and a human lung cancer cell.

14. An improved composition for treating a resistant tumor cell in a mammal which comprises a tumor suppressing amount of a cytostatic hydrophobic chemotherapeutic agent, a multidrug resistance reversing agent and a nontoxic pharmaceutically acceptable carrier, wherein the multidrug resistant reversing agent is a macrocyclic lactone compound selected from the group consisting of LL-F28249α-λ, a 23-oxo derivative of LL-F28249α-λ, a 23-imino derivative of LL-F28249α-λ, an avermectin, a 22,23-dihydro derivative of avermectin and a milbemycin.

15. The composition according to claim 14, wherein the chemotherapeutic agent is selected from the group consisting of vinblastine, vincristine, doxorubicin, paclitaxel, colchicine, actinomycin D and gramicidin D.

* * * * *